US008450080B2

(12) United States Patent
Bajad et al.

(10) Patent No.: US 8,450,080 B2
(45) Date of Patent: May 28, 2013

(54) METHODS OF MONITORING METABOLIC PATHWAYS

(75) Inventors: Sunil Bajad, Emeryville, CA (US); Michael Leavell, Emeryville, CA (US)

(73) Assignee: Amyris, Inc., Emeryville, CA (US)

( * ) Notice: Subject to any disclaimer, the term of this patent is extended or adjusted under 35 U.S.C. 154(b) by 905 days.

(21) Appl. No.: 12/361,478

(22) Filed: Jan. 28, 2009

(65) Prior Publication Data

US 2009/0203019 A1 Aug. 13, 2009

Related U.S. Application Data

(60) Provisional application No. 61/063,258, filed on Jan. 31, 2008.

(51) Int. Cl.
*C12Q 1/02* (2006.01)
*G01N 33/53* (2006.01)

(52) U.S. Cl.
USPC .................................... 435/29; 435/7.91

(58) Field of Classification Search
USPC ................................... 435/29, 7.91
See application file for complete search history.

(56) References Cited

U.S. PATENT DOCUMENTS

| 7,172,886 | B2 | 2/2007 | Keasling et al. |
| 7,183,089 | B2 | 2/2007 | Keasling et al. |
| 7,192,751 | B2 | 3/2007 | Keasling et al. |
| 2004/0058995 | A1 | 3/2004 | Shinohara et al. |
| 2006/0121558 | A1 | 6/2006 | Stephanopoulos et al. |

FOREIGN PATENT DOCUMENTS

WO   WO 2005/033287   4/2005

OTHER PUBLICATIONS

Link et al. (Leakage of adenylates during cold methanol/glycerol quenching of *Escheria coli*. Metabolomics (2008) 4:240-247).*
Boas et al. (Cold glycerol-saline: The promising quenching solution for accurate intracellular metabolite analysis of microbial cells.).*
Bajad et al. "Separation and quantitation of water soluble cellular metabolites by hydrophilic interaction chromatography-tandem mass spectrometry," Journal of Chromatography A, 2006, vol. 1125(1), pp. 76-88.
Bochar et al., "Sequence comparisons reveal two classes of 3-hydroxy-3-methylglutaryl coenzyme A reductase," Mol. Genet Metab., 1999, vol. 66(2), pp. 122-127.
Coulier et al, "Simultaneous Quantitative Analysis of Metabolites Using Ion-Pair Liquid Chromatography—Electrospray Ionization Mass Spectrometry," Anal. Chem., 2006, vol. 78(18), pp. 6573-6582.
Farmer et al., "Precursor balancing for metabolic engineering of lycopene production in *Escherichia coli*.," Biotechnol. Prog., 2001, vol. 17(1), pp. 57-61.
Gonzalez-Pacanowska et al, "Isopentenoid Synthesis in Isolated Embryonic *Drosophila* Cells. Farnesol catabolism and omega-oxidation," The Journal of Biological Chemistry, 1988, vol. 263(3), pp. 1301-1306.
Hedl et al., "Class II 3-hydroxy-3-methylglutaryl coenzyme A reductases," J. Bacteriology, 2004, vol. 186(7), pp. 1927-1932.
Kajiwara et al., "Expression of an exogenous isopentenyl diphosphate isomerase gene enhances isoprenoid biosynthesis in *Escherichia coli*," Biochem. J., 1997, vol. 324, pp. 421-426.
Kim et al., "Metabolic engineering of the nonmevalonate isopentenyl diphosphate synthesis pathway in *Escherichia coli* enhances lycopene production," Biotechnol. Bioeng, 2001, vol. 72(4), pp. 408-415.
Korz et al., "Simple fed-batch technique for high cell density cultivation of *Escherichia coli*," Journal of Biotechnology, 1995, vol. 39(1), pp. 59-65.
Lange et al., "Isoprenoid biosynthesis: the evolution of two ancient and distinct pathways across genomes," Proc. Natl. Acad. Sci. USA, 2000, vol. 97(24), pp. 13172-13177.
Martin et al, "Engineering a Melvonate Pathway in *Eschericia coli* for production of terpinoids," Nature Biotechnology, 2003, vol. 21(7), pp. 796-802.
McCaskill et al, "Procedures for the Isolation and Quantification of the Intermediates of the Melvonic Acid Pathway," Analytical Biochemistry, 1993, vol. 215(1), pp. 142-149.
Rohmer et al., "Isoprenoid biosynthesis in bacteria: a novel pathway for the early steps leading to isopentenyl diphosphate," Biochem. J., 1993, vol. 295, pp. 517-524.
Rohdich et al. "Studies on the nonmevalonate terpene biosynthetic pathway: metabolic role of IspH (LytB) protein," Proc.Natl. Acad. Sci. USA, 2002, vol. 99(3), pp. 1158-1163.
Ruijter et al, "Determination of intermediary metabolites in *Aspergillus niger*," Journal of Microbiological Methods, 1996, vol. 25, pp. 295-302.
Seker et al, "Analysis of acyl CoA ester intermediates of the mevalonate pathway in *Saccharomyces cerevisia*," Appl Microbiol Biotechnol, 2005, vol. 67(1), pp. 119-124.
International Search Report for PCT Application No. PCT/US09/32249, mailed Jun. 2, 2009.
Written Opinion for PCT Application No. PCT/US09/32249, mailed Jun. 2, 2009.
International Preliminary Report on Patentability for PCT Application No. PCT/US09/32249, mailed Aug. 12, 2010.

* cited by examiner

*Primary Examiner* — Karen Cochrane Carlson
*Assistant Examiner* — Natalie Moss
(74) *Attorney, Agent, or Firm* — Morgan, Lewis & Bockius LLP

(57) ABSTRACT

The present invention provides methods and compositions for monitoring cofactors and metabolites of a metabolic pathway of interest. The subject compositions and methods are particularly suited for monitoring the mevalonate pathway in a variety of cells. The invention also provides fermentation methods for the production of isoprenoids.

17 Claims, 14 Drawing Sheets

METHODS OF MONITORING METABOLIC PATHWAYS

PRIOR RELATED APPLICATION

This application claims the benefit under 35. U.S.C. §119 (e) of U.S. Provisional Application No. 61/063,258 filed Jan. 31, 2008 which is incorporated herein in its entirety.

BACKGROUND

Isoprenoids are ubiquitous in nature. They comprise a diverse family of over 40,000 individual products, many of which are vital to living organisms. Isoprenoids serve to maintain cellular fluidity, electron transport, and other metabolic functions. A vast number of natural and synthetic isoprenoids are useful as pharmaceuticals, cosmetics, perfumes, pigments and colorants, fungicides, antiseptics, nutraceuticals, and fine chemical intermediates.

An isoprenoid product is typically composed of repeating five carbon isopentenyl diphosphate (IPP) units, although irregular isoprenoids and polyterpenes have been reported. In nature, isoprenoids are synthesized by consecutive condensations of their precursor IPP and its isomer dimethylallyl pyrophosphate (DMAPP). Two pathways for these precursors are known. Eukaryotes, with the exception of plants, generally use the mevalonate-dependent (MEV) pathway to convert acetyl coenzyme A (acetyl-CoA) to IPP, which is subsequently isomerized to DMAPP. Prokaryotes, with some exceptions, typically employ only the mevalonate-independent or deoxyxylulose-5-phosphate (DXP) pathway to produce IPP and DMAPP. Plants use both the MEV pathway and the DXP pathway. See Rohmer et al. (1993) *Biochem. J.* 295:517-524; Lange et al. (2000) *Proc. Natl. Acad. Sci. USA* 97(24):13172-13177; Rohdich et al. (2002) *Proc. Natl. Acad. Sci. USA* 99:1158-1163.

Traditionally, isoprenoids have been manufactured by extraction from natural sources such as plants, microbes, and animals. However, the yield by way of extraction is usually very low due to a number of profound limitations. First, most isoprenoids accumulate in nature in only small amounts. Second, the source organisms in general are not amenable to the large-scale cultivation that is necessary to produce commercially viable quantities of a desired isoprenoid. Third, the requirement of certain toxic solvents for isoprenoid extraction necessitates special handling and disposal procedures, and thus complicating the commercial production of isoprenoids.

The elucidation of the MEV and DXP metabolic pathways has made biosynthetic production of isoprenoids feasible For instance, microbes have been engineered to overexpress a part of or the entire mevalonate pathway for production of an isoprenoid named amorpha-4,11-diene (U.S. Pat. Nos. 7,172,886 and 7,192,751) Other efforts have focused on balancing the pool of glyceraldehyde-3-phosphate and pyruvate, or on increasing the expression of 1-deoxy-D-xylulose-5-phosphate synthase (dxs) and IPP isomerase (idi). See Farmer et al. (2001) *Biotechnol. Prog.* 17:57-61; Kajiwara et al. (1997) *Biochem. J.* 324:421-426; and Kim et al. (2001) *Biotechnol. Bioeng.* 72:408-415. Nevertheless, the conventional methods for monitoring and quantitation of metabolite levels in cells that utilize the mevalonate pathway suffer from a number of profound drawbacks. First, the conventional methods can only monitor a very limited number of the cofactors and metabolites involved in the mevalonate pathway. Second, this limitation is exacerbated by the fact that metabolites and individual cofactors of the pathway exhibit varying chemical stability profiles, which has made extraction and quantitation of more than several of such metabolites and cofactors difficult to achieve. There thus remains a need for methods and compositions useful for monitoring metabolic pathways such as the mevalonate pathway. The present invention addresses this need and provides related advantages as well.

SUMMARY OF THE INVENTION

The present invention provides compositions and methods related to the monitoring of mevalonate pathway metabolites. In one embodiment, the invention provides a method of quantitating a cofactor and a mevalonate pathway metabolite, comprising (a) providing an extract of a cell comprising said cofactor and said mevalonate pathway metabolite, wherein the extract exhibits a pH value of greater than about 7; and (b) quantitating said cofactor and said metabolite from said extract. In another embodiment, the invention provides a method of quantitating a cofactor and a mevalonate pathway metabolite, comprising (a) providing an extract of a cell comprising said cofactor and said mevalonate pathway metabolite, wherein the extract exhibits a pH value of greater than about 7; (b) dividing said extract of (a) into a plurality of aliquots, one of which being analyzed to quantitate individual metabolites of the mevalonate pathway except acetoacetyl-CoA, and to quantitate individual cofactors; and (c) adding an acid to at least one other aliquot, wherein said at least one other aliquot is analyzed to quantitate acetoacetyl CoA.

The cofactor may be selected from a first group consisting of $NAD^+$, $NADP^+$, NADH, NADPH, AMP, ADP, and ATP. The metabolite may be selected from a second group consisting of CoA metabolite and non-CoA metabolite. Non-CoA metabolites include farnesyl pyrophosphate, geranyl pyrophosphate, isopentenyl pyrophosphate, dimethylallyl pyrophosphate, mevalonate, mevalonate phosphate, and mevalonate pyrophosphate. CoA metabolites include acetyl CoA, acetoacetyl-CoA, and 3-hydroxy-3-methylglutaryl-CoA.

In some embodiments, the methods quantitate all cofactors and metabolites of the mevalonate pathway. In other embodiments, the step of quantitating is by mass spectrometry. For example, the step of quantitating may be by liquid chomatography in conjunction with mass spectrometry.

The invention also provides a method of quantitating all cofactors involved in the mevalonate pathway and all mevalonate pathway metabolites, comprising (a) providing an extract of a cell comprising said all cofactors and said all metabolites, wherein said extract comprises a buffer that stabilizes said cofactors and metabolites for at least about 8 hours; and (b) quantitating said all cofactors involved in the mevalonate pathway and said all metabolites from said extract. The cofactors may be $NAD^+$, $NADP^+$, NADH, NADPH, AMP, ADP, and ATP, and said all metabolites may be Acetyl CoA, Acetoacetyl-CoA, 3-hydroxy-3-methylglutaryl-CoA, farnesyl pyrophosphate, geranyl pyrophosphate, isopentenyl pyrophosphate, dimethylallyl pyrophosphate, mevalonate, mevalonate phosphate, and mevalonate pyrophosphate.

The invention also provides an extract from a cell comprising a cofactor and a mevalonate pathway metabolite, wherein the extract exhibits a pH value greater than about 9 and comprises an alcohol, and wherein the cofactor and the metabolite are stable in said extract for at least about 8 hours. The cofactor and the metabolite may also be stable in said extract for at least about 12 hours. In some cases, the alcohol is methanol. When desired, the extract is quenched at a temperature below 0° C. In certain embodiments, the extract is quenched at a temperature below −23° C.

Also provided herein is a fermentation method, comprising: (a) initiating a first fermentation reaction comprising a medium and a population of host cells under an initial fermentation condition suitable for producing an isoprenoid from mevalonate pathway; (b) simultaneously quantitating a cofactor and a mevalonate pathway metabolite from the first fermentation reaction, wherein said cofactor and said metabolite are produced by said host cells; (c) performing a second fermentation reaction wherein one or more parameters of the initial fermentation condition used during the first fermentation reaction is adjusted based on the amount of said cofactor and/or said metabolite quantitated in (b). In some embodiments, the one or more parameters of (c) support production of said isoprenoid at a level higher than that produced under said initial fermentation condition. In one embodiment, the cell is prokaryotic or bacterial. Alternatively, the cell is eukaryotic. For example, the cell can be a yeast cell. The isoprenoid may be, for example, an alcohol. In some embodiments, the isoprenoid is a hydrocarbon.

The present invention additionally describes a method of quantitating a plurality of types of mevalonate pathway metabolites, comprising: (a) providing an extract of a cell comprising said plurality of types of mevalonate pathway metabolites, wherein a first type of metabolite in said plurality is CoA mevalonate pathway metabolite selected from the group consisting of Acetyl-CoA, Acetoacetyl-CoA, and 3-hydroxy-3-methylglutaryl-CoA, and wherein a second type of metabolite in said plurality is non-CoA mevalonate pathway metabolite selected from the group consisting of farnesyl pyrophosphate, geranyl pyrophosphate, isopentenyl pyrophosphate, dimethylallyl pyrophosphate, mevalonate, mevalonate phosphate, and mevalonate pyrophosphate; and (b) quantitating said plurality of types of mevalonate pathway metabolites from said extract.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE INVENTION

Definitions

Figure 1:
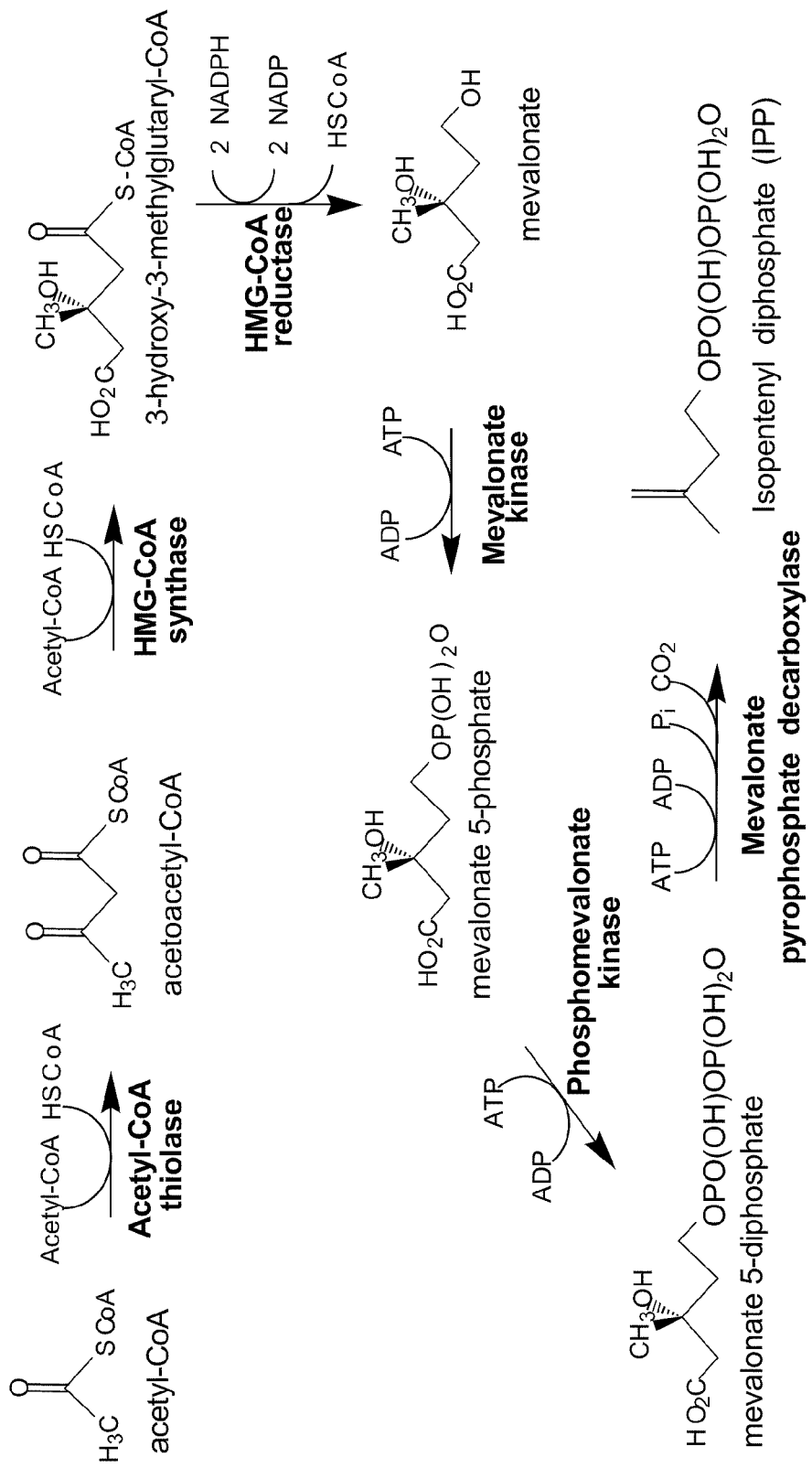
FIG. 1 is a schematic representation of the mevalonate ("MEV") pathway for the production of isopentenyl pyrophosphate ("IPP").
Figure 2:
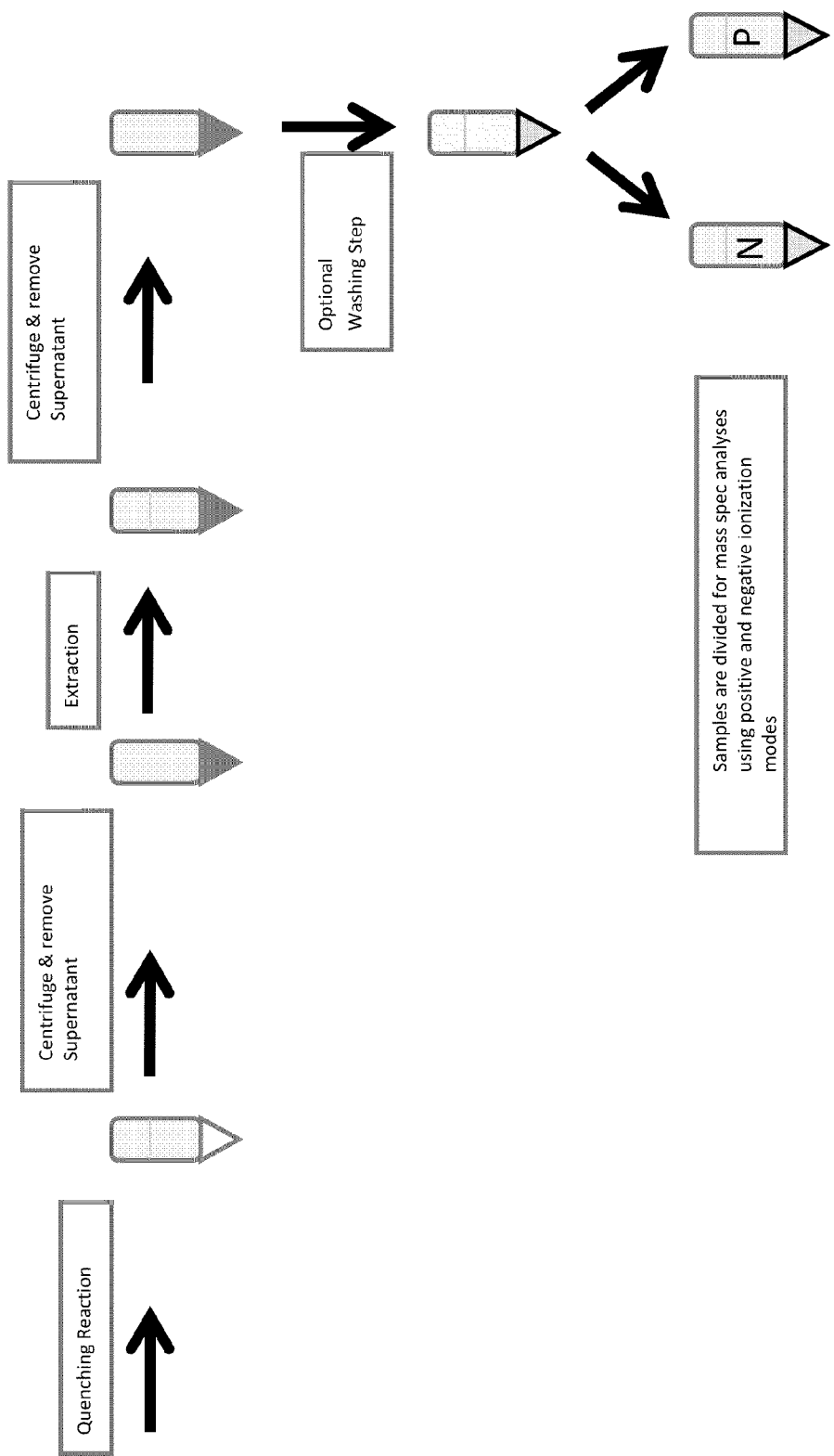
FIG. 2 is a schematic illustrating one embodiment of the inventive method comprising a quenching step; extraction step; and an optional washing step. The samples are divided into two aliquots which are treated in different manners for mass spectrometry analysis using positive and negative ionization modes. This allows for the detection and quantification of MEV pathway metabolites and co-factors.

Unless defined otherwise, all technical and scientific terms used herein have the same meaning as commonly understood by one of ordinary skill in the art to which this invention belongs. Reference is made here to a number of terms that shall be defined to have the following meanings:

The term "optional" or "optionally" means that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where the event or circumstance does not occur.

The terms "metabolic pathway" is used herein to refer to a catabolic pathway or an anabolic pathway. Anabolic pathways involve constructing a larger molecule from smaller molecules, a process requiring energy. Catabolic pathways involve breaking down of larger molecules, often releasing energy. The term "mevalonate pathway" or "MEV pathway" is used herein to refer to the biosynthetic pathway that converts acetyl-CoA to IPP. The MEV pathway is illustrated schematically in FIG. 1.

The term "mevalonate pathway metabolite" includes precursors, intermediates and products of the mevalonate pathway. "CoA mevalonate pathway metabolites" include Acetyl-CoA, Acetoacetyl-CoA and 3-hydroxy-3-methylglutaryl-CoA. "Non-CoA mevalonate pathway metabolites" include other mevalonate pathway metabolites such as farnesyl pyrophosphate, geranyl pyrophosphate, isopentenyl pyrophosphate, dimethylallyl pyrophosphate, mevalonate, mevalonate phosphate, and mevalonate pyrophosphate.

The term "cofactor" refers to a nonprotein component which participates in an enzymatic reaction. Cofactors which are involved in the mevalonate pathway include, but are not limited to, adenosine monophosphate (AMP), adenosine diphosphate (ADP), adenosine triphosphate (ATP), nicotinamide adenine dinucleotide ($NAD^+$, NADH) and nicotinamide adenine dinucleotide phosphate ($NADP^+$, NADPH). Acetyl-CoA is both a cofactor and a CoA mevalonate pathway metabolite.

The term "extract" refers to a cell product obtained from a cell or collection of cells, for example a prokaryotic or eukaryotic cell culture. An extract may comprise intracellular and extracellular components of a cell, as well as parts of the fluid or solid medium in which the cell has been grown, as well as any buffers or additional reagents that may be used in the extraction procedure. Extracts are commonly liquids, solids, or may be liquids comprising solid fragments such as cellular fractions or precipitates.

The terms "cell", "host cell" or "host microorganism" are used interchangeably. They refer to any archae, eukaryotic or prokaryotic organisms comprising at least part of the mevalonate pathway. Such organisms may be naturally occurring or may be genetically modified by insertion of a vector expressing a desired nucleic acid or polypeptide sequence or a vector comprising a sequence to alter the expression of a polypeptide endogenous to the host cell.

The term "aliquot" refers to a fraction of an extract isolated at any step during an extraction procedure.

The term "quantitate" refers to the action of measuring any relative or absolute concentration of a compound.

The term "relative standard deviation", "RSD" or "% RSD" is a measure of the precision of an assay and represents to the absolute value of the coefficient of variation expressed as a percentage. It is generally calculated as RSD=(standard deviation of a range of samples)*100/(mean of range of samples).

The term "pH value" expresses the degree of acidity or basicity of a solution. In general, the term "acidifying" refers to a step in which an acidic solution is added to another solution to lower the initial pH value, resulting in a solution which may be acidic, neutral or even basic, depending on the amount of acidic solution added. Similary, "basifying" refers to a step in which a basic solution is added to another solution to raise the initial pH value, resulting in a solution which may be basic, neutral or even acidic, depending on the amount of basic solution added.

The word "pyrophosphate" is used interchangeably herein with "diphosphate".

The term "endogenous" refers to a substance or process that occurs naturally, e.g., in a non-recombinant host cell.

The terms "nucleic acid" and "polynucleotide" are used interchangeably. They refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically, or biochemically modified, non-natural, or derivatized nucleotide bases.

The term "protein", "polypeptides" and "peptides" are used interchangeably. They refer to a polymeric form of amino acids of any length, which can include coded and non-coded amino acids, chemically or biochemically modified or derivatized amino acids, and polypeptides having modified peptide backbones. The term "naturally occurring" as applied to a nucleic acid, an enzyme, a cell, or an organism, refers to a nucleic acid, enzyme, cell, or organism that is found in nature. For example, a polypeptide or polynucleotide sequence that is present in an organism that can be isolated from a source in nature and that has not been intentionally modified by a human in the laboratory is naturally occurring.

The terms "isoprenoid", "isoprenoid compound", "isoprenoid product", "terpene", "terpene compound", "terpenoid", and "terpenoid compound" are used interchangeably herein. They refer to compounds that are capable of being derived from IPP.

The singular forms "a," "and," and "the" include plural referents unless the context clearly dictates otherwise. Thus, for example, reference to "an expression vector" includes a single expression vector as well as a plurality of expression vectors, and reference to "the host cell" includes reference to one or more host cells, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Unless otherwise indicated, this invention is not limited to particular compounds, cofactors, intermediates, metabolites, enzymes, microorganisms, or processes, and as such may vary in accordance with the understanding of those of ordinary skill in the arts to which this invention pertains in view of the teaching herein. Terminology used herein is for purposes of describing particular embodiments only and is not intended to be limiting.

Cells

Any suitable cell may be used in the practice of the present invention. Illustrative examples of suitable cells include any archae, prokaryotic, or eukaryotic cell that comprises the entire or part of the mevalonate pathway. Examples of an archae cell include, but are not limited to those belonging to the genera: *Aeropyrum, Archaeglobus, Halobacterium, Methanococcus, Methanobacterium, Pyrococcus, Sulfolobus,* and *Thermoplasma*. Illustrative examples of archae strains include but are not limited to: *Aeropyrum pernix, Archaeoglobus fulgidus, Methanococcus jannaschii, Methanobacterium thermoautotrophicum, Pyrococcus abyssi, Pyrococcus horikoshii Thermoplasma acidophilum, Thermoplasma volcanium.*

Examples of a procaryotic cell include, but are not limited to those belonging to the genera: *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphlococcus, Strepromyces, Synnecoccus,* and *Zymomonas*.

Illustrative examples of prokaryotic bacterial strains include but are not limited to: *Bacillus subtilis, Bacillus amyloliquefacines, Brevibacterium ammoniagenes, Brevibacterium immariophilum, Clostridium beigerinckii, Enterobacter sakazakii, Escherichia coli, Lactococcus lactis, Mesorhizobium loti, Pseudomonas aeruginosa, Pseudomonas mevalonii, Pseudomonas pudica, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei, Staphylococcus aureus,* and the like.

In general, if a bacterial host cell is used, a non-pathogenic strain is generally preferred. Illustrative examples of non-pathogenic strains include but are not limited to: *Bacillus subtilis, Escherichia coli, Lactibacillus acidophilus, Lactobacillus helveticus, Pseudomonas aeruginosa, Pseudomonas mevalonii, Pseudomonas pudita, Rhodobacter sphaeroides, Rodobacter capsulatus, Rhodospirillum rubrum,* and the like.

Examples of eukaryotic cells include but are not limited to fungal cells. Examples of fungal cell include, but are not limited to those belonging to the genera: *Aspergillus, Candida, Chrysosporium, Cryotococcus, Fusarium, Kluyveromyces, Neotyphodium, Neurospora, Penicillium, Pichia, Saccharomyces, Trichoderma* and *Xanthophyllomyces* (formerly *Phaffia*).

Illustrative examples of eukaryotic strains include but are not limited to: *Aspergillus nidulans, Aspergillus niger, Aspergillus oryzae, Candida albicans, Chrysosporium lucknowense, Fusarium graminearum, Fusarium venenatum,*

*Kluyveromyces lactis, Neurospora crassa, Pichia angusta, Pichia finlandica, Pichia kodamae, Pichia membranaefaciens, Pichia methanolica, Pichia opuntiae, Pichia pastoris, Pichia pijperi, Pichia quercuum, Pichia salictaria, Pichia thermotolerans, Pichia trehalophila, Pichia stipitis, Streptomyces ambofaciens, Streptomyces aureofaciens, Streptomyces aureus, Saccaromyces bayanus, Saccaromyces boulardi, Saccharomyces cerevisiae, Streptomyces fungicidicus, Streptomyces griseochromogenes, Streptomyces griseus, Streptomyces lividans, Streptomyces olivogriseus, Streptomyces rameus, Streptomyces tanashiensis, Streptomyces vinaceus, Trichoderma reesei* and *Xanthophyllomyces dendrorhous* (formerly *Phaffia rhodozyma*).

In general, if a eukaryotic cell is used, a non-pathogenic strain is preferred. Illustrative examples of non-pathogenic strains include but are not limited to: *Fusarium graminearum, Fusarium venenatum, Pichia pastoris, Saccaromyces boulardi*, and *Saccaromyces cerevisiae.*

In addition, certain strains have been designated by the Food and Drug Administration as GRAS or Generally Regarded As Safe. These strains include: *Bacillus subtilis, Lactibacillus acidophilus, Lactobacillus helveticus*, and *Saccharomyces cerevisiae.*

In one embodiment, the cell is a genetically modified host microorganism in which nucleic acid molecules have been inserted, deleted or modified (i.e., mutated; e.g., by insertion, deletion, substitution, and/or inversion of nucleotides), to either produce the desired isoprenoid compound or isoprenoid derivative, or effect an increased yield of the desired isoprenoid compound or isoprenoid derivative. In another embodiment, the host cell is capable of being grown in liquid growth medium. In contrast, a "control cell" is an alternative subject or sample used in an experiment for comparison purpose, and is typically a parental cell that does not contain the modification(s) made to a corresponding host cell.

Isoprenoid Pathways

In one embodiment, the cells of the present invention typically comprise or utilize the MEV pathway, and possibly the DXP pathway to synthesize IPP and its isomer, DMAPP. In general, eukaryotes other than plants use the MEV isoprenoid pathway exclusively to convert acetyl-CoA to IPP, which is subsequently isomerized to DMAPP. Prokaryotes, with some exceptions, use the mevalonate-independent or DXP pathway to produce IPP and DMAPP separately through a branch point. In general, plants use both the MEV and DXP pathways for IPP synthesis.

A schematic representation of the MEV pathway is described in FIG. 1. In the first step, two molecules of acetyl-coenzyme A are enzymatically combined to form acetoacetyl-CoA. An enzyme known to catalyze this step is, for example, acetyl-CoA thiolase (also known as acetyl-CoA acetyltransferase). In the second step of the MEV pathway, acetoacetyl-CoA is enzymatically condensed with another molecule of acetyl-CoA to form 3-hydroxy-3-methylglutaryl-CoA (HMG-CoA). An enzyme known to catalyze this step is, for example, HMG-CoA synthase. In the third step, HMG-CoA is enzymatically converted to mevalonate. An enzyme known to catalyze this step is, for example, HMG-CoA reductase. In the fourth step, mevalonate is enzymatically phosphorylated to form mevalonate 5-phosphate. An enzyme known to catalyze this step is, for example, mevalonate kinase.

In the fifth step, a second phosphate group is enzymatically added to mevalonate 5-phosphate to form mevalonate 5-pyrophosphate. An enzyme known to catalyze this step is, for example, phosphomevalonate kinase.

In the sixth step, mevalonate 5-pyrophosphate is enzymatically converted into IPP. An enzyme known to catalyze this step is, for example, mevalonate pyrophosphate decarboxylase. If IPP is to be converted to DMAPP, then a seventh step is required. An enzyme known to catalyze this step is, for example, IPP isomerase. If the conversion to DMAPP is required, an increased expression of IPP isomerase ensures that the conversion of IPP into DMAPP does not represent a rate-limiting step in the overall pathway.

In some embodiments, the host cell produces IPP via the MEV pathway, either exclusively or in combination with the DXP pathway. In other embodiments, a host's DXP pathway is functionally disabled so that the host cell produces IPP exclusively through a heterologously introduced MEV pathway. The DXP pathway can be functionally disabled by disabling gene expression or inactivating the function of one or more of the DXP pathway enzymes.

The metabolites DMAPP and IPP can undergo further reactions to produce additional metabolites. For example, the enzyme farnesyl pyrophosphate synthase can catalyze sequential condensation reactions of dimethylallyl pyrophosphate with 2 units of 3-isopentenyl pyrophosphate to form farnesyl pyrophosphate (FPP). In the first step, DMAPP may react with IPP to form geranyl pyrophosphate (GPP). Subsequently, one molecule of GPP may react with IPP to form one molecule of FPP. Below are described additional metabolites which may be produced by the mevalonate pathway.

Measurement of Cofactors and MEV Pathway Metabolites

The metabolites and the cofactors involved in the mevalonate pathway have a wide spectrum of physiochemical properties which makes quantification of these components problematic. For example, these compounds can be phosphorylated (mono, di, or tri) or non-phosphorylated. They also span the range from hydrophobic to hydrophilic. Certain metabolites such as isopentenyl pyrophosphate, dimethylallyl phyrophosphate, farnesyl pyrophosphate, NADPH and NADH are unstable in acidic solvents whereas ATP and CoAs are more stable in acidic solvents. Because of the complications involved, simultaneous analyses of these metabolites have not been previously attempted. Surprisingly, extraction of the cell metabolites in an extraction solvent with a pH greater than about 7, allows for the detection of all cofactors and metabolites.

Thus in one aspect, a method is provided comprising:
 a. providing an extract of a cell comprising said cofactor and said mevalonate pathway metabolite, wherein the extract exhibits a pH value of greater than about 7; and
 b. quantitating said cofactor and said metabolite from said extract.

In certain embodiments, the cell extract exhibits a pH value greater than or equal to about 8. In other embodiments, the cell extract exhibits a pH value greater than or equal to about 9. In still other embodiments, the cell extract exhibits a pH value greater than or equal to about 9.4.

In some embodiments, the cell extract exhibits a pH value of between 8 and 13. In some embodiments, the cell extract exhibits a pH value of between 8 and 11. In some embodiments, the cell extract exhibits a pH value of between 8 and 10. In some embodiments, the cell extract exhibits a pH value of between 9 and 13. In some embodiments, the cell extract exhibits a pH value of between 9 and 12. In some embodiments, the cell extract exhibits a pH value of between 9 and 11. In some embodiments, the cell extract exhibits a pH value of between 9 and 10.

In some embodiments, the pH of the cell extract is due to the addition of an extraction solvent having a pH value greater than about 7. In certain embodiments, the pH of the cell extract is due to the addition of an extraction solvent having a pH value greater than or equal to about 8. In other embodiments, the pH of the cell extract is due to the addition of an extraction solvent having a pH value greater than or equal to about 9. In still other embodiments, the pH of the cell extract is due to the addition of an extraction solvent having a pH value greater than or equal to about 9.4.

In some embodiments, the pH of the cell extract is due to the addition of an extraction solvent having a pH value of between 7 and 13. In some embodiments, the pH of the cell extract is due to the addition of an extraction solvent having a pH value of between 7 and 10. In some embodiments, the pH of the cell extract is due to the addition of an extraction solvent having a pH value of between 7 and 9. In some embodiments, the pH of the cell extract is due to the addition of an extraction solvent having a pH value of between 8 and 13. In some embodiments, the pH of the cell extract is due to the addition of an extraction solvent having a pH value of between 8 and 11. In some embodiments, the pH of the cell extract is due to the addition of an extraction solvent having a pH value of between 8 and 10. In some embodiments, the pH of the cell extract is due to the addition of an extraction solvent having a pH value of between 9 and 13. In some embodiments, the pH of the cell extract is due to the addition of an extraction solvent having a pH value of between 9 and 11. In some embodiments, the pH of the cell extract is due to the addition of an extraction solvent having a pH value of between 9 and 10.

In other embodiments, the extraction solvent comprises an alcohol and a basic buffer. In certain embodiments, the alcohol is a $C_1$-$C_5$ alcohol. In certain other embodiments, the alcohol is methanol or ethanol. Any suitable basic buffer can be used. Such a buffer may comprise cationic and anionic species such that the buffering capacity is sufficient around the desired pH. Illustrative examples of suitable cationic species include an ammonium salt such as ammonium chloride, ammonium acetate, and the like. The ratio of alcohol to basic buffer can be about 1. An illustrative example is a 1:1 solution of alcohol such as methanol to basic buffer such as ammonium acetate. In other embodiments, the ration of alcohol to basic buffer is greater than 2. An illustrative example is a solution comprising 70% methanol and 30% basic buffer such as ammonium acetate.

In one embodiment, the cofactor is NADH and/or NADPH. In another embodiment, the cofactor is ATP, ADP, AMP or any combination thereof. In still other embodiments, the mevalonate pathway metabolite is a CoA mevalonate pathway metabolite such as Acetyl-CoA, Acetoacetyl-CoA or 3-hydroxy-3-methylglutaryl-CoA. In yet another embodiment, the mevalonate pathway metabolite is Acetoacetyl-CoA or 3-hydroxy-3-methylglutaryl-CoA.

In another embodiment, the mevalonate pathway metabolite is IPP or DMAPP. In yet another embodiment, the mevalonate pathway metabolite is mevalonate, mevalonate phosphate or mevalonate pyrophosphate. In still another embodiment, all cofactors from the group consisting of $NAD^+$, $NADP^+$, NADH, NADPH, AMP, ADP, and ATP are quantitated. In other embodiments, all metabolites from the group consisting of Acetyl-CoA, Acetoacetyl-CoA, 3-hydroxy-3-methylglutaryl-CoA, farnesyl pyrophosphate, geranyl pyrophosphate, isopentenyl pyrophosphate, dimethylallyl pyrophosphate, mevalonate, mevalonate phosphate, and mevalonate pyrophosphate are quantitated.

In another embodiment, the invention provides a method of quantitating a plurality of types of mevalonate pathway metabolites, including a first and second type of metabolites. The first type of metabolite may be a CoA mevalonate pathway metabolite, including Acetyl-CoA, Acetoacetyl-CoA, and 3-hydroxy-3-methylglutaryl-CoA, and the second type of metabolite may be a non-CoA mevalonate pathway metabolite, including farnesyl pyrophosphate, geranyl pyrophosphate, isopentenyl pyrophosphate, dimethylallyl pyrophosphate, mevalonate, mevalonate phosphate and mevalonate pyrophosphate.

In another aspect, a method is provided comprising:
a. quenching cell metabolism in a plurality of cells having at least one cofactor and metabolite by contacting the cells with a quenching solvent resulting in a first mixture, wherein the first mixture has a temperature that is equal to or less than about −25° C.;
b. adding an extraction solvent to the first mixture resulting in a second mixture wherein the pH of the second mixture has a pH value greater than about 7; and
c. quantitating said cofactor and said metabolite from the second mixture.

In some embodiments, the quenching solvent is a liquid at about −80° C. In other embodiments, the quenching solvent comprises methanol. In still other embodiments, the quenching solvent comprises methanol and glycerol. In certain other embodiments, the quenching solvent comprises methanol and glycerol and remains a liquid at −80° C.

In other embodiments, the temperature of the first mixture is less than about −23° C. In certain other embodiments, the temperature of the first mixture is equal to or less than about −30° C. In still other embodiments, the temperature of the first mixture is less than about −30° C.

In still other embodiments, the first mixture is centrifuged to separate the cells from the quenching solvent. When this is the case, the first mixture comprises the resulting cell pellet.

In certain embodiments, the second mixture exhibits a pH value greater than or equal to about 8. In other embodiments, the second mixture exhibits a pH value greater than or equal to about 9. In still other embodiments, the second mixture exhibits a pH value greater than or equal to about 9.4.

In certain embodiments, the second mixture exhibits a pH value between 8 and 13. In certain embodiments, the second mixture exhibits a pH value between 8 and 11. In certain embodiments, the second mixture exhibits a pH value between 8 and 10. In certain embodiments, the second mixture exhibits a pH value between 9 and 13. In certain embodiments, the second mixture exhibits a pH value between 9 and 11. In certain embodiments, the second mixture exhibits a pH value between 9 and 10.

In certain other embodiments, the pH of the second mixture is due to the addition of an extraction solvent having a pH value greater than about 7. In certain embodiments, the pH of the second mixture is due to the addition of an extraction solvent having a pH value greater than or equal to about 8. In other embodiments, the pH of the second mixture is due to the addition of an extraction solvent having a pH value greater than or equal to about 9. In still other embodiments, the pH of the second mixture is due to the addition of an extraction solvent having a pH value greater than or equal to about 9.4.

In certain other embodiments, the pH of the second mixture is due to the addition of an extraction solvent having a pH value between about 7 and 13. In certain other embodiments, the pH of the second mixture is due to the addition of an extraction solvent having a pH value between about 7 and 11. In certain other embodiments, the pH of the second mixture is due to the addition of an extraction solvent having a pH value between about 7 and 9. In certain other embodiments, the pH of the second mixture is due to the addition of an extraction solvent having a pH value between about 8 and 13. In certain other embodiments, the pH of the second mixture is due to the addition of an extraction solvent having a pH value between about 8 and 11. In certain other embodiments, the pH of the second mixture is due to the addition of an extraction solvent having a pH value between about 8 and 10. In certain other embodiments, the pH of the second mixture is due to the addition of an extraction solvent having a pH value between about 9 and 13. In certain other embodiments, the pH of the second mixture is due to the addition of an extraction solvent having a pH value between about 9 and 11. In certain other embodiments, the pH of the second mixture is due to the addition of an extraction solvent having a pH value between about 9 and 10.

Additional processing steps to improve quantification include breaking open the cells to allow the cofactor and metabolite into the solution of the second mixture. Any method known in the art can be used to break open the cells such as vortexing and sonication or a combination of both. In some embodiments, glass beads can be used to facilitate by mechanical means to break open the cells. Other processing steps can include centrifugation to remove unwanted cell debris from the supernatant.

The second mixture can be divided into a plurality of aliquots so that each aliquot can be subsequently processed different to stabilize certain metabolites. As used herein, "stable" or "stabilized" refers to at least 50% of the initial concentration of a cofactor or metabolite remaining in an extract in a given time period. Cofactors and metabolites described in the invention are be stable for at least 1, 2, 3, 4, 5, 7, 8, 16, or 24 hours. In some embodiments, the cofactors involved in the mevalonate pathway and mevalonate pathway metabolites are stable for at least about 8 hours. In other embodiments, the cofactors and the metabolites are stable for at least about 12 hours.

In certain embodiments, at least one of these aliquots is acidified to stabilize CoAs and ATP. In other embodiments, at least one of these aliquots is acidified to stabilize CoAs. In still other embodiments, at least one of these aliquots is acidified to stabilize ATP. In yet other embodiments, at least one of these aliquots is acidified to stabilize acetoacetyl-CoA. Any suitable acid which can acidify an otherwise basic solution can be added to at least one of the aliquots of the second mixture. Prior to quantification, the plurality of aliquots can then be diluted as necessary with a suitable solvent such as methanol to optimize the concentrations of the cofactors and metabolites in the sample for analyses.

In another aspect, a method is provided comprising:
a. quenching cell metabolism in a plurality of cells having at least one cofactor and metabolite by contacting the cells with a quenching solvent resulting in a first mixture, wherein the first mixture has a temperature that is equal to or less than about $-25°$ C.;
b. separating the cells from the supernatant in the first mixture resulting in a cell pellet;
c. isolating the cell pellet;
d. adding an extraction solvent to the cell pellet resulting in a second mixture wherein the pH of the second mixture has a pH value greater than about 8;
e. breaking open the cells in the second mixture;
f. separating the cell debris from the supernatant in the second mixture;
g. dividing the supernatant in the second mixture into at least two aliquots;
h. acidifying one of the at least two aliquots; and,
i. quantitating the at least one cofactor and metabolite in the at least two aliquots.

In some embodiments, the at least one cofactor and metabolite includes a CoA or ATP. In other embodiments, the at least one cofactor and metabolite includes a CoA. In still other embodiments, the at least one cofactor and metabolite includes acetoacetyl CoA.

Quantification may be by any method known in the art. In some embodiments, liquid chromatography is used. Numerous elution buffers, columns and parameters are known in the art, and may be used to perform the method of the invention. In one embodiment, an aminopropyl column is used. In another embodiment, one of the buffers used as an eluting buffer comprises ammonium acetate.

In other embodiments, mass spectrometry is used to identify and quantitate the compounds of the invention. In certain embodiments, MS/MS is used to quantitate peaks isolated by liquid chromatography (see Bajad et al, Journal of Chromatography A, 1125 (2006) 76-88). In still other embodiments, isotopically labeled internal standards are used to quantify each compound of interest.

In certain embodiments of the invention, any of the cofactors or mevalonate pathway metabolites, or any combination of cofactors, CoA and non-CoA mevalonate pathway metabolites are quantitated with a relative standard deviation of less than 30%, 25%, 20%, 17%, 13% or 10%. In other embodiments, the RSD is less than 13%. In still other embodiments, the RSD is less than 30%. Relative standard deviation may refer to values measured from samples produced from the same extract. Alternatively, the relative standard deviation may refer to values measured from samples produced from different extracts.

In another aspect, an extract from a cell is provided comprising: a cofactor and a mevalonate pathway metabolite, wherein the extract exhibits a pH value greater than about 9 and comprises an alcohol, and wherein the cofactor and the metabolite are stable in said extract for at least about 8 hours. The cofactor and the metabolite may also be stable in said extract for at least about 12 hours. In some cases, the alcohol is methanol. When desired, the extract is quenched at a temperature below $0°$ C. In certain embodiments, the extract is quenched at a temperature below $-23°$ C.

In yet another aspect, a fermentation method is provided comprising: (a) initiating a first fermentation reaction comprising a medium and a population of host cells under an initial fermentation condition suitable for producing an isoprenoid from mevalonate pathway; (b) simultaneously quantitating a cofactor and a mevalonate pathway metabolite from the first fermentation reaction, wherein said cofactor and said metabolite are produced by said host cells; (c) performing a second fermentation reaction wherein one or more parameters of the initial fermentation condition used during the first fermentation reaction is adjusted based on the amount of said cofactor and/or said metabolite quantitated in (b). In some embodiments, the one or more parameters of (c) support production of said isoprenoid at a level higher than that produced under said initial fermentation condition. In one embodiment, the cell is prokaryotic or bacterial. Alternatively, the cell is eukaryotic. For example, the cell can be a yeast cell. The isoprenoid may be, for example, an alcohol. In some embodiments, the isoprenoid is a combustible molecule.

The methods of the invention may be used in combination with other methods of determining an enzymatic activity of a given pathway enzyme or concentration of certain mevalonate pathway metabolites. In general, the enzymatic activity can be ascertained by the formation of the product or conversion of a substrate of an enzymatic reaction that is under investigation. The reaction can take place in vitro or in vivo. For example, the relative activity of HMG-CoA reductase and HMG-CoA synthase in a cell can be measured by the steady state level of HMG-CoA in a cell. HMG-CoA can be extracted by Tricholoroacetic Acid (TCA), followed by analyzing the extracted material via Liquid Chromatography/Mass Spectrometry. The activity of mevalonate kinase can be demonstrated by the formation of mevalonate 5-phosphate. The relative activity of mevalonate kinase and HMG-CoA reductase can be measured by the steady state level of mevalonate, which can be determined by Gas Chromatography/Mass spectrometry. See e.g., WO05033287, which is incorporated herein by reference.

Fermentation

The present invention provides fermentation methods comprising initiating a fermentation reaction comprising a medium and a population of host cells under an initial fermentation condition suitable for producing an isoprenoid from the mevalonate pathway, quantitating simultaneously a cofactor and a mevalonate pathway metabolite produced by the host cells, and subsequently adjusting one or more parameters of the initial fermentation condition based on the amount, relative ratio or concentration of any cofactors and/or metabolites quantitated.

Parameters of fermentation condition which may be adjusted or left unchanged include, but are not limited to, selection of medium, medium supplements, nutrients, vitamins, minerals, nitrogen or $CO_2$ content, temperature, feed rate, choice of reactor, choice of organism to be used as host cell, and duration of incubation. Genetic modification is also encompassed as such a parameter, and any of the methods and biological molecules for engineering pathways discussed in this application may be employed. In one embodiment, any parameter may be modified which can affect the yield or efficiency of production of an isoprenoid compound, or which may result in a fermentation condition which is superior to the initial condition. In one such embodiment, such a parameter supports production of an isoprenoid at a level which is higher than that shown under initial fermentation conditions.

Any cells described herein can be utilized in the subject fermentation method. In some embodiments, the host cell expresses a nucleic acid sequence encoding a mevalonate pathway enzyme from a prokaryote having an endogenous mevalonate pathway. Non-limiting examples of suitable prokaryotes include those from the genera: *Actinoplanes; Archaeoglobus; Bdellovibrio; Borrelia; Chloroflexus; Enterococcus; Lactobacillus; Listeria; Oceanobacillus; Paracoccus; Pseudomonas; Staphylococcus; Streptococcus; Streptomyces; Thermoplasma*; and *Vibrio*. Non-limiting examples of specific strains include: *Archaeoglobus fulgidus; Bdellovibrio bacteriovorus; Borrelia burgdorferi; Chloroflexus aurantiacus; Enterococcus faecalis; Enterococcus faecium; Lactobacillus johnsonii; Lactobacillusplantarum; Lactococcus lactis; Listeria innocua; Listeria monocytogenes; Oceanobacillus iheyensis; Paracoccus zeaxanthinifaciens; Pseudomonas mevalonii; Staphylococcus aureus; Staphylococcus epidermidis; Staphylococcus haemolyticus; Streptococcus agalactiae; Streptomyces griseolosporeus; Streptococcus mutans; Streptococcus pneumoniae; Streptococcus pyogenes; Thermoplasma acidophilum; Thermoplasma volcanium; Vibrio cholerae; Vibrioparahaemolyticus*; and *Vibrio vulnificus;*

In another embodiment, the nucleic acid sequence encoding a mevalonate pathway enzyme is selected from acetyl-CoA thiolase, HMG-CoA synthase, HMG-CoA reductase, and mevalonate kinase. In another embodiment, the nucleic acid sequence encoding a mevalonate pathway enzyme is selected from acetyl-CoA thiolase, HMG-CoA synthase, HMG-CoA reductase, and mevalonate kinase and is from a prokaryote belonging to the genus *Enterococcus* or the genus *Pseudomonas* or the genus *Staphylococcus*. In another embodiment, the nucleic acid sequence encoding a mevalonate pathway enzyme is selected from acetyl-CoA thiolase, HMG-CoA synthase, HMG-CoA reductase, and mevalonate kinase and is from *Enterococcus faecalis* or from *Staphylococcus aureus*.

In another embodiment, nucleic acid sequence encoding a mevalonate pathway enzyme is a Class II HMG-CoA reductase. HMG-CoA reductases are generally classified into two classes, which are distinguishable based on sequence homology and/or enzymatic properties (see, for example, Hedl, et al., J. Bacteriology, 1927 1932, 2004, and Bochar, et al., Molec. Genet. Metab., 66, 122-127, 1999).

A prototypical Class II HMG-CoA reductase is derived from *Pseudomonas mevalonii*. Also encompassed in the invention are variant Class II HMG-CoA reductases exhibiting at least about 30%, 35%, 40%, 45%, 50%, 55%, 60%, 65%, 70%, 80%, 90%, or 95% identity as compared to the amino acid sequence of *P. mevalonii* HMG-CoA reductase. Further encompassed in the invention are variants having less than about 40%, 35%, 30%, 25%, 20%, or less, identity with an *H. Sapiens* HMG-CoA reductase. The identities of amino acid sequences can be determined by the methods described in Bochar, et al., Molec. Genet. Metab., 66, 122-127, 1999.

Non-limiting exemplary Class II HMG-CoA reductases include those derived from HMG-CoA reductases from: *Archaeoglobus fulgidus* (NC_000917); *Bdellovibrio bacteriovorus* (BX842650); *Borrelia burgdorferi* (AE001169); *Chloroflexus aurantiacus* (AJ299212); *Enterococcus faecalis* (AAO81155); *Enterococcus faecium* (AF290094); *Lactobacillus johnsonii* (AE017204); *Lactobacillus plantarum*; *Lactococcus lactis* (AE006387); *Listeria innocua* (CAC96053); *Listeria monocytogenes* (AE017324); *Oceanobacillus iheyensis* (NC_000917); *Paracoccus zeaxanthinifaciens* (AJ431696); *Pseudomonas mevalonii* (M24015); *Staphylococcus aureus* (AF290086); *Staphylococcus epidermidis* (AF290090); *Staphylococcus haemolyticus* (AF290088); *Streptococcus agalactiae* (CAD47046); *Streptomyces griseolosporeus* (AB037907); *Streptococcus mutans* (AAN58647); *Streptococcus pneumoniae* (AF290098); *Streptococcus pyogenes* (AF290096); *Thermoplasma acidophilum* (CAC 11548); *Thermoplasma volcanium* (AL935253); *Vibrio cholerae* (AAF96622); *Vibrio parahaemolyticus* (BAC62311); and *Vibrio vulnificus* (AA007090).

In other embodiments, the host cells are cultured in a fermentation medium comprises a carbon source present in an amount that is lower than that which would provide for a maximum specific growth rate. In certain embodiments, the host cells are cultured in a medium where the carbon source is maintained at a level to provide for less than about 90%, 80%, 75%, 60%, 50%, 40%, 30%, 25%, 20%, 10%, 5%, 1%, or less, of the maximum specific growth rate. Any carbon-containing sources that are digestible by the microorganism can be used. Non-limiting examples include carbohydrates such as monosaccharides, oligosaccharides and polysaccharides, organic acids such as acetic acid, propionic acid; and alcohols such as ethanol and propanol, and polyols such as glycerol.

In some embodiments, the carbon sources comprise primarily monosaccharides or oligosaccharides. In other embodiments, the carbon source consists essentially of monosaccharides and disaccharides. In still other embodiments, the carbon source is essentially free of cellulose.

Monosaccharides are the simple sugars that serve as building blocks for carbohydrates. They are classified based on their backbone of carbon (C) atoms: trioses have three carbon atoms, tetroses four, pentoses five, hexoses six, and heptoses seven. The carbon atoms are bonded to hydrogen atoms (—H), hydroxyl groups (—OH), and carbonyl groups (—C═O), whose combinations, order, and configurations allow a large number of stereoisomers to exist. Pentoses include xylose, found in woody materials; arabinose, found in gums from conifers; ribose, a component of RNA and several vitamins, and deoxyribose, a component of DNA. Exemplary hexoses include glucose, galactose, and fructose. Monosaccharides combine with each other and other groups to form a variety of disaccharides, and oligosaccharides. An oligosaccharide is a saccharide polymer containing a small number (typically three to ten) of simple sugars. They are generally found either O- or N-linked to compatible amino acid side chains in proteins or lipid moieties. A preferred oligosaccharide for use in the present fermentation reaction is disaccharide, including for example, sucrose, or trisaccharide such as raffinose.

Where it is desired to have cellulose, glycan, starch, or other polysaccharides as the ultimate carbon source, these polysaccharides can be first converted into monosaccharides and oligosaccharides by chemical means or by enzymatic methods. For instance, cellulose can be converted into glucose by the enzyme cellulase. Accordingly, if polysaccharides such as cellulose found in the biomass (including e.g., canola, alfalfa, rice, rye, sorghum, sunflower, wheat, soybean, tobacco, potato, peanut, cotton, sweet potato, cassava, coffee, coconut, citrus trees, cocoa, tea, fruits such as, banana, fig, pineapple, guava, mango, oats, barley, vegetables, ornamentals, or conifers) is used as the ultimate carbon source, it can be digested by cellulase to generate simpler sugars for use in conjunction with the fermentation procedure of the present invention. In certain embodiments, after the breakdown of the polysaccharide, the monosaccharide and/or oligosaccharide constitute at least about 50% by weight of the carbon source as determined at the beginning of the fermentation. In other embodiments, the monosaccharide and/or oligosaccharide constitute at least about 80% or even 90% by weight of the carbon source as determined at the beginning of the fermentation, such that the fermentation medium is essentially free of cellulose.

In other embodiments, the host cells are cultured in a fermentation medium comprises a nitrogen source. Sources of assimilable nitrogen that can be used in a suitable fermentation reaction mixture include, but are not limited to, simple nitrogen sources, organic nitrogen sources, and complex nitrogen sources. Such nitrogen sources include anhydrous ammonia, ammonium salts of inorganic or organic acids such as ammonium chloride, ammonium sulfate, ammonium acetate, ammonium phosphate, other nitrogen-containing compounds and substances of animal, vegetable, and/or microbial origin. Amino acids can also be used as the nitrogen source, including leucine, isoleucine or valine, or a mixture thereof.

In other embodiments, the fermentation reaction is given an initial bolus of carbon source sufficient to grow at or near the maximum specific growth rate (unlimited growth) followed by a reduced feed rate at a level below that required to support the maximum specific growth rate, for the remainder of the fermentation. In some cases, the point at which the reduced carbon source feed rate is implemented is the point at which a predetermined feed rate is achieved. In certain embodiments, the microorganism is provided with enough carbon source to grow exponentially to a feed rate of about 15 g/L/hr, after which the feed rate is reduced to 5.7 g/L/hr and held constant at that rate for the remainder of the fermentation.

In certain embodiments, one or more of the heterologous mevalonate pathway enzymes is inducible and induced after the carbon source feed rate has been reduced to a level below that required for maximum specific growth. For example, where the engineered microorganism has an inducible promoter, the fermentation is first run by adding carbon source to achieve a exponential growth, but at a level which is below that to support maximum specific growth, then the carbon source feed rate is reduced to an even lower level for the remainder of the fermentation, and the inducer added after the carbon source feed rate is reduced. In some embodiments, the microorganisms are induced with isopropylthio-beta-D-galactoside (IPTG) after the reduced carbon source feed is initiated.

In other embodiments, the fermentation reaction is performed in a manner that avoids the build up of toxic substances that decrease cell growth rates. For example, it is known that when too much glucose is added to the medium, toxic products such as acetate can build up in the organism. See, for example, Kortz et al. (1995) *J. Biotechnol.* 39: 59-65. Thus by providing a high level of carbon source, at or approaching the amount which would support a maximum growth rate (unlimited growth), the initial growth of the cells may be higher, but the growth becomes arrested due to the accumulation of toxic substances. The level at which the carbon source is added below the level where the toxic products do not accumulate is referred to as the critical level or the inhibitory threshold. Thus in certain embodiments, the fermentation reaction is performed such that the carbon source is kept below the critical level for the build up of toxic substances. Those skilled in the art will appreciate that the critical concentration of substrates will vary with the strain and the medium which is used.

An effective fermentation reaction mixture can contain other compounds such as inorganic salts, vitamins, trace metals, or growth promoters. Such other compounds can also be present in carbon, nitrogen or mineral sources in the effective reaction mixture or can be added specifically to the reaction mixture. One embodiment of the invention involves providing these compounds at levels that are suboptimal as compared to that would support the maximum growth rate of the host cells in order to increase isoprenoid production.

The fermentation reaction mixture can also contain a suitable phosphate source. Such phosphate sources include both inorganic and organic phosphate sources. Non-limiting examples of phosphate sources include, but are not limited to, phosphate salts such as mono or dibasic sodium and potassium phosphates, ammonium phosphate, polyphosphate, and mixtures thereof. A suitable fermentation reaction mixture can also include a source of magnesium. In some embodiments, the magnesium is in the form of a physiologically acceptable salt, such as magnesium sulfate heptahydrate, although other magnesium sources in concentrations that contribute similar amounts of magnesium can be used. Further, in some instances it may be desirable to allow the fermentation reaction mixture to become depleted of a magnesium source during fermentation.

The fermentation reaction mixture can also include a biologically acceptable chelating agent, such as the dihydrate of trisodium citrate and ethylenediaminetetraacetic acid. The fermentation reaction mixture can also initially include a biologically acceptable acid or base to maintain the desired pH of the fermentation reaction mixture. Biologically acceptable acids include, but are not limited to, hydrochloric acid, sulfuric acid, nitric acid, phosphoric acid and mixtures thereof. Biologically acceptable bases include, but are not limited to, ammonium hydroxide, sodium hydroxide, potassium hydroxide and mixtures thereof.

The fermentation reaction mixture can also include a biologically acceptable calcium source, including, but not limited to, calcium chloride. The fermentation reaction mixture can also include sodium chloride. The fermentation reaction mixture can also include trace metals. Such trace metals can be added to the fermentation reaction mixture as a stock solution that, for convenience, can be prepared separately from the rest of the fermentation reaction mixture. A suitable trace metals solution can include, but is not limited to sodium selenate; ferrous sulfate; heptahydrate; cupric sulfate, pentahydrate; zinc sulfate, heptahydrate; sodium molybdate, dihydrate; cobaltous chloride; selenium or chromium solution; hexahydrate; and manganous sulfate monohydrate. Hydrochloric acid may be added to the stock solution to keep the trace metal salts in solution.

If a pathway intermediate or a compound that can be converted to a pathway intermediate is added to the fermentation medium, the intermediate or compound is typically present in an excess amount.

Fermentation can be conducted under anaerobic (deficient in oxygen) or aerobic (oxygenated) conditions. Under aerobic conditions, microorganisms can break down sugars to end products such as $CO_2$ and $H_2O$. Under anaerobic conditions, the host cells utilize an alternative pathway to produce $CO_2$ and ethanol. Fermentation can also be used to refer to the bulk growth of microorganisms on a growth medium where no distinction is made between aerobic and anaerobic metabolism. In general, aerobic fermentation is carried out for production of isoprenoids.

The fermentations of the present invention can be carried out in a batch, a fed-batch, or a continuous process. A batch process is typically a closed process where all of the raw materials are added at the beginning of the fermentation. A fed-batch process is typically a closed process where the carbon source and/or other substrates are added in increments throughout the process. A fed-batch process allows for greater control of the medium and the growth of the microorganisms. A continuous process can be considered an open system where medium is continuously added and product is simultaneously removed. Processes in between these types can also be used. For instance, in one embodiment, the fermentation is begun as a fed-batch process, and an organic layer, such as dodecane is placed in contact with the fermentation medium while the fermentation process continues. Isoprenoids, which typically have a higher solubility in the organic medium than in the aqueous fermentation medium are extracted out of the fermentation medium into the organic layer. Where the isoprenoids are produced in excess of the saturation point and form a layer separable from the medium, then simple separation by way of draining or sucking the distinct phase layer can be carried out. This process has characteristics of both a fed-batch process and a continuous process, because of the removal of product from the medium and the fermentation progresses. The fed-batch and continuous processes allow for the control of the addition of fermentation components during the fermentation process. A fed-batch, continuous, or combination of these processes is usually preferred in carrying out the invention. Thee processes allow for greater control of the rate of addition of feed and other fermentation components as a function of time. The removal of product during fermentation can be beneficial, especially where the accumulated product leads to inhibition of the production pathways.

The amount of microorganism per liter of fermentation, or the density of microorganism, can be measured by measuring the weight of microorganism isolated from a given volume of the fermentation medium. A common measure is the dry weight of cells per liter of fermentation medium. Another method which can be used to monitor the fermentation while it is progressing is by a measurement of the optical density of the medium. A common method is to measure the optical density at a wavelength of 600 nm, referred to the $OD_{600}$, or the OD. The OD can be correlated to a the density of a specific type of organism within a specific medium, but the specific relationship between OD and amount of microorganism per volume will not generally be applicable across all types of organisms in all types of media. A calibration curve can be created by measuring the OD and the dry cell weight over a range of cell densities. In some cases, these correlations can be used in different fermentation of the same or similar microorganisms in the same or similar media.

The subject fermentation methods are suitable for producing a wide variety of isoprenoids.

Non-limiting examples of suitable isoprenoids include: hemiterpenes (derived from 1 isoprene unit) such as isoprene; monoterpenes (derived from 2 isoprene units) such as myrcene; sesquiterpenes (derived from 3 isoprene units) such as amorpha-4,1-diene; diterpenes (derived from four isoprene units) such as taxadiene; triterpenes (derived from 6 isoprene units) squalene; tetraterpenes (derived from 8 isoprenoids) β-carotene; and polyterpenes (derived from more than 8 isoprene units) such as polyisoprene. In some embodiments, the isoprenoid is not a carotenoid. In other embodiments, the isoprenoid is a $C_5$-$C_{20}$ isoprenoid.

$C_5$ compounds may be derived from IPP or DMAPP. These compounds are also known as hemiterpenes because they are derived from a single isoprene unit (IPP or DMAPP).

Isoprene, whose structure is

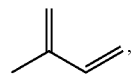

is found in many plants and is made from IPP by isoprene synthase.

$C_{10}$ compounds may be derived from geranyl pyrophosphate (GPP), which is made by the condensation of IPP with DMAPP. An enzyme known to catalyze this step is, for example, geranyl pyrophosphate synthase. These $C_{10}$ compounds are also known as monoterpenes because they are derived from two isoprene units. GPP can be further processed to a monoterpene. GPP is then subsequently converted to a variety of $C_{10}$ compounds. Illustrative examples of $C_{10}$ compounds include but are not limited to:

Carene, whose structure is

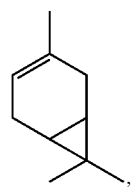

is found in the resin of many trees, particularly pine trees. Carene is made from GPP from carene synthase.

Geraniol (also known as rhodnol), whose structure is

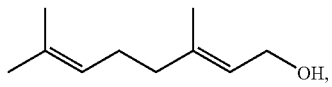

is the main component of oil-of-rose and palmarosa oil. It also occurs in geranium, lemon, and citronella. Geraniol is made from GPP by geraniol synthase.

Linalool, whose structure is

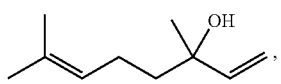

is found in many flowers and spice plants such as coriander seeds. Linalool is made from GPP by linalool synthase.

Limonene, whose structure is

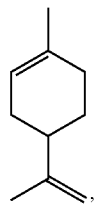

is found in the rind of citrus fruits and peppermint. Limonene is made from GPP by limonene synthase.

Myrcene, whose structure is

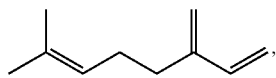

is found in the essential oil in many plants including bay, verbena, and myrcia from which it gets its name. Myrcene is made from GPP by myrcene synthase.

α- and β-Ocimene, whose structures are

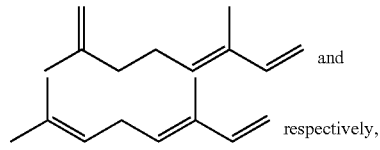

are found in a variety of plants and fruits including *Ocimum basilicum* and is made from GPP by ocimene synthase.

α-Pinene, whose structure is

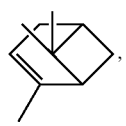

is found in pine trees and eucalyptus. α-Pinene is made from GPP by α-pinene synthase. β-Pinene β-Pinene, whose structure is

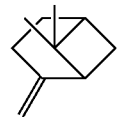

is found in pine trees, rosemary, parsley, dill, basil, and rose. β-Pinene is made from GPP by β-pinene synthase.

Sabinene, whose structure is

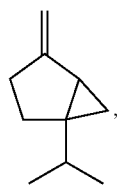

is found in black pepper, carrot seed, sage, and tea trees. Sabinene is made from GPP by sabinene synthase.

γ-Terpinene, whose structure is

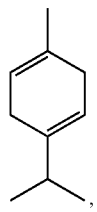

is a constituent of the essential oil from citrus fruits. Biochemically, γ-terpinene is made from GPP by a γ-terpinene synthase.

Terpinolene, whose structure is

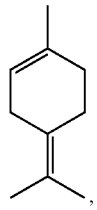

is found in black currant, cypress, guava, lychee, papaya, pine, and tea. Terpinolene is made from GPP by terpinolene synthase.

$C_{15}$ compounds may be derived from farnesyl pyrophosphate (FPP) which is made by the condensation of two molecules of IPP with one molecule of DMAPP. An enzyme known to catalyze this step is, for example, farnesyl pyrophosphate synthase. These $C_{15}$ compounds are also known as sesquiterpenes because they are derived from three isoprene units. Illustrative examples of $C_{15}$ compounds include but are not limited to:

Amorphadiene, whose structure is

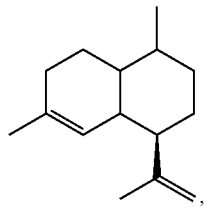

is a precursor to artemisinin which is made by *Artemisia anna*. Amorphadiene is made from FPP by amorphadiene synthase.

α-Farnesene, whose structure is

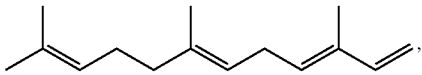

is found in various biological sources including but not limited to the Dufour's gland in ants and in the coating of apple and pear peels. α-Farnesene is made from FPP by α-farnesene synthase.

β-Farnesene, whose structure is

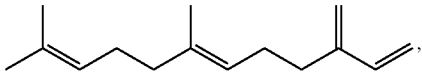

is found in various biological sources including but not limited to aphids and essential oils such as from peppermint. In some plants such as wild potato, β-farnesene is synthesized as a natural insect repellent. β-Farnesene is made from FPP by β-farnesene synthase.

Farnesol, whose structure is

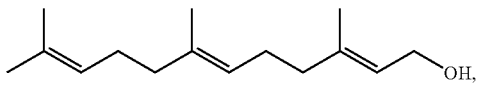

is found in various biological sources including insects and essential oils such as from cintronella, neroli, cyclamen, lemon grass, tuberose, and rose. Farnesol is made from FPP by a hydroxylase such as farnesol synthase.

Nerolidol, whose structure is

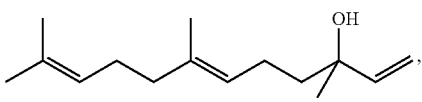 [SMILES: C=CC(C)(O)CC/C=C(\C)CCC=C(C)C]

is also known as peruviol, and is found in various biological sources including as essential oils such as from neroli, ginger, jasmine, lavender, tea tree, and lemon grass. Nerolidol is made from FPP by a hydroxylase such as nerolidol synthase.

Patchoulol, whose structure is

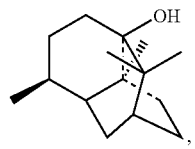

is also known as patchouli alcohol and is a constituent of the essential oil of Pogostemonpatchouli. Patchouliol is made from FPP by patchouliol synthase.

Valencene, whose structure is

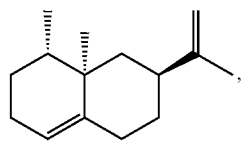

is one of the main chemical components of the smell and flavour of oranges and is found in orange peels. Valencene is made from FPP by nootkatone synthase.

$C_{20}$ compounds may be derived from geranylgeraniol pyrophosphate (GGPP) which is made by the condensation of three molecules of IPP with one molecule of DMAPP. An enzyme known to catalyze this step is, for example, geranylgeranyl pyrophosphate synthase. These $C_{20}$ compounds are also known as diterpenes because they are derived from four isoprene units. GGPP can be further processed to a diterpene, or can be further processed to produce a carotenoid. Alternatively, GGPP can also be made by adding IPP to FPP. GGPP is then subsequently converted to a variety of $C_{20}$ isoprenoids. Illustrative examples of $C_{20}$ compounds include but are not limited to:

Geranylgeraniol, whose structure is

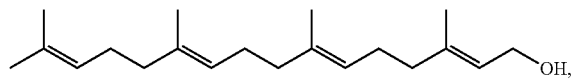

is a constituent of wood oil from *Cedrela toona* and of linseed oil. Geranylgeraniol can be made by e.g., adding to the expression constructs a phosphatase gene after the gene for a GGPP synthase.

Abietadiene encompasses the following isomers:

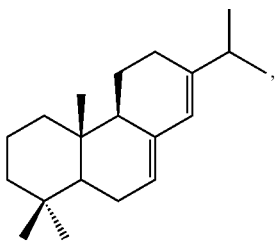

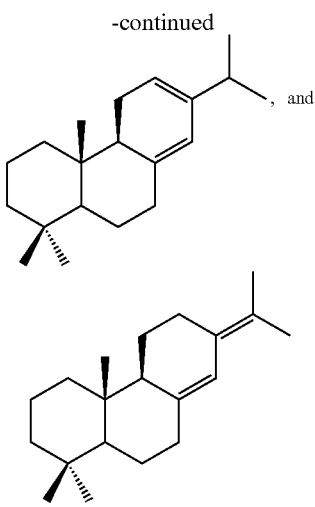

and is found in trees such as *Abies grandis*. Abietadiene is made by abietadiene synthase. Illustrative examples of C$_{20+}$ compounds include sesterterpenes (C$_{25}$ compound made from five isoprene units), triterpenes (C$_{30}$ compounds made from six isoprene units), and tetraterpenes (C$_{40}$ compound made from eight isoprene units).

In some embodiments, the fermentation methods of the invention may be used in the production of a combustible isoprenoid. The isoprenoid compounds described herein may, for example, be used as combustible materials or fuels.

Engineering Pathways

In some embodiments of the invention, the fermentation methods of the invention comprise adjusting a parameter of the initial fermentation condition by engineering MEV pathways to enhance production of isoprenoids in a host cell. The pathway is typically engineered via recombinant DNA technology by expressing heterologous sequences encoding enzymes in the pathway. The activity of a MEV pathway enzyme in a host can be altered in a number of ways, including, but not limited to, expressing a modified form of the enzyme that exhibits increased solubility in the host cell, expressing an altered form of the enzyme that lacks a domain through which the activity of the enzyme is inhibited, expressing a modified form of the enzyme that has a higher K$_{cat}$ or a lower K$_m$ for the substrate, or expressing an altered form of the enzyme that is not affected by feed-back or feed-forward regulation by another molecule in the pathway. Such variant enzymes can also be isolated through random mutagenesis of a broader specificity enzyme, as described below, and a nucleotide sequence encoding such variant enzyme can be expressed from an expression vector or from a recombinant gene integrated into the genome of a host microorganism.

The yield of an isoprenoid via one or more metabolic pathways disclosed herein can be augmented by inhibiting reactions that divert intermediates from productive steps towards formation of the isoprenoid product. Inhibition of the unproductive reactions can be achieved by reducing the expression and/or activity of enzymes involved in one or more unproductive reactions. Such reactions include side reactions of the TCA cycle that lead to fatty acid biosynthesis, alanine biosynthesis, the aspartate superpathway, gluconeogenesis, heme biosynthesis, and/or glutamate biosynthesis, at a level that affects the overall yield of an isoprenoid production. Additionally, the conversion of acetyl-CoA to acetate via the action of phosphotransacetylase is another example of unproductive side reaction. Therefore, where desired, "knocking out" or "knocking down" the pta gene that encodes phosphotransacetylase may also be carried in order to increase the yield of isoprenoid production. Depending on the specific isoprenoid of interest, one skilled in the art may choose to target additional unproductive steps. For example, where carotenoid is the isoprenoid of choice, one may opt to "knock out" or "knock down" one or more genes selected from the group consisting of gdhA, acee, fdhF, yjiD, hnr or yjfP, ackA, appY, aspC, clp, clpP, clpXP, crcB, csda, cyaA, evgS, fdhA, fdhD, feoB, fuma, glnE, glxR, gntK, hycI, lipB, lysU, modA, moeA, nada, nuoC, nuoK, pflB, pitA, pst, pstC, pta, p-yjiD, sohA, stpA, yagR, yaiD, ybas, ycfz, ydeN, yebB, yedN, yfcc, ygiP, yibD, yjfP, yjhH, or yliE genes, or any other genes alone or in combination, the inhibition of which would result in a higher yield of carotenoid as described in U.S. Patent Application 20060121558, which is incorporated herein by reference.

A variety of methods are available for knocking out or knocking down a gene of interest. For example, a reduced gene expression may be accomplished by deletion, mutation, and/or gene rearrangement. It can also be carried out with the use of antisense RNA, siRNA, miRNA, ribozymes, triple stranded DNA, and transcription and/or translation inhibitors. In addition, transposons can be employed to disrupt gene expression, for example, by inserting it between the promoter and the coding region, or between two adjacent genes to inactivate one or both genes.

Although the invention has been described in conjunction with specific embodiments thereof, the foregoing description is intended to illustrate and not limit the scope of the invention. Other aspects, advantages, and modifications within the scope of the invention will be apparent to those skilled in the art to which the invention pertains.

EXAMPLES

The practice of the present invention can employ, unless otherwise indicated, conventional techniques of the biosynthetic industry and the like, which are within the skill of the art. To the extent such techniques are not described fully herein, one can find ample reference to them in the scientific literature.

The following examples are intended for illustrative purposes only and do not limit in any way the scope of the present invention. Variations and modifications to the following exemplary protocols and procedures are contemplated so long as they support quantitation of a cofactor and a metabolic pathway metabolite, or they support quantitation of a plurality of types of metabolites of a given pathway.

Example 1

LC/MS/MS was used to evaluate a set of standards representing mevalonate pathway metabolites and co-factors. The objective was to verify that both the metabolites and co-factors can be detected using the desired LC/MS/MS procedure.

Study Design. Standards of the mevalonate pathway metabolite and co-factors were prepared and analyzed using LC/MS/MS and used to determine expected retention times. Metabolites were analyzed using P and N modes as mentioned below.

Buffer Preparation. Ammonium Acetate Buffer—38.5 g ammonium acetate was added to 500 mL of 1 M Ammonium acetate in LC/MS grade water. The mixture was transferred to a 500 mL graduated cylinder. Water was added to make up 500 mL and the buffer was stored at 4° C. for future use.

1 M Ammonium Hydroxide Buffer −17.5 g was added to HPLC grade water to a volume of 500 mL and stored at 4° C. for future use.

LC Solvent—To a clean LC solvent bottle and fresh pipettes, 960 mL of LC/MS grade water, 20 mL of ammonium acetate solution, and 20 mL of ammonium hydroxide solution was added. After the additions, the solution was mixed well. 50 mL of solvent was removed and transferred to a 50 mL falcon tube and stored at 4° C. for preparation of the extraction buffer. 50 mL acetonitrile was added to the LC solvent and the solution was mixed again.

Internal Standards—2 mg/mL stock solution for each internal standard was prepared in 50:50 MeOH:$H_2O$ buffer except for mevalonate. A stock solution of mevalonate was prepared in 50:50 MeOH: 20 mM ammonium acetate buffer (pH 9.4).

MeOH with Formic Acid-0.1 mL of 100% formic acid was added to 79.9 mL of LC/MS grade methanol and stored at 4° C.

Extraction Buffer-25 mL of LC solvent prepared above was added to 25 mL of LC/MS grade methanol. The solution was mixed well and stored at 4° C.

Run Conditions

HPLC Parameters are shown in Table 1.

TABLE 1

HPLC Parameters

| Parameter | Value |
|---|---|
| Mobile phase A | 20 mM ammonium acetate buffer with 5% acetonitrile |
| Mobile phase B | Acetonitrile |
| Column | Aminopropyl |
| Column Temp | 25° C. |
| Flow Rate | 0.2 mL/min |
| Injection Volume | 20 μL |
| Autosampler temperature | 4° C. |
| Gradient | 0 min = 80% B |

LC gradient

| Time (min) | Solvent B (%) |
|---|---|
| 0 | 80 |
| 25 | 20 |
| 30 | 20 |
| 30.01 | 80 |
| 37 | End run |

Mass Spectrometer Parameters are shown in Table 2.

TABLE 2

Mass Spectrometer Parameters

| Parameter | Value |
|---|---|
| Spray voltage | 3500 V (positive ionization mode) 3000 V (negative ionization mode) |
| Capillary temperature | 350° C. |
| Sheath gas | 45 arbitrary units |
| Aux gas | 15 arbitrary units |
| Vaporizer temp | 0 |
| Collision gas | 1.5 Torr |
| SRM scan width | 1 |
| SRM scan time | 0.1 sec |
| Micro scans | 2 |

Metabolite and Internal Standard SRMS

The SRM values for the metabolites and co-factors analyzed are shown in Table 3

TABLE 3

Metabolite and Internal Standard SRMS

| | Parent ion mass | Product ion mass | Collision energy (eV) |
|---|---|---|---|
| Positive ionization mode | | | |
| AMP | 348 | 136 | 21 |
| $^{13}C^{15}N$ AMP (Internal standard for AMP) | 363.1 | 146 | 21 |
| FAD | 786 | 348 | 24 |
| AcetylCoA | 810 | 303 | 28 |
| AcetoacetylCoA | 852 | 345 | 34 |
| $^{13}C$ MalonylcoA (Internal standard for CoA's and FAD) | 857 | 305 | 30 |
| 3 HMGCoA | 910 | 408 | 43 |
| Negative ionization mode | | | |
| Mevalonate | 147 | 59 | 15 |
| Mevalonate additional SRM | 147 | 41 | 30 |
| $D_7$ mevalonate (Internal standard for mevalonate) | 154 | 59 | 15 |
| Mevalonate P | 227 | 79 | 20 |
| IPP/DMAPP | 245 | 79 | 20 |
| Mevalonate PP | 307 | 79 | 20 |
| GPP | 313 | 79 | 18 |
| FPP | 382 | 79 | 21 |
| ADP | 426 | 134 | 24 |
| $^{13}C^{15}N$ TTP (Internal standard for all the metabolites monitored in negative mode except mevalonate) | 493 | 159 | 31 |
| ATP | 506 | 408 | 21 |
| NAD | 662 | 540 | 19 |
| NADH | 664 | 408 | 31 |
| NADP | 742 | 620 | 18 |
| NADPH | 744 | 408 | 34 |

Results. Each mevalonate metabolite and co-factor was detected as shown by the data in FIG. 3 using LC/MS/MS. LC/MS/MS using P and N mode analysis allows for simultaneous detection and identification of the mevalonate pathway metabolites and co-factors. Usage of an aminopropyl column allows for analyte separate with defined peak shapes.

Example 2

S. cerevisiae or E. coli was grown in either shake flasks or fermentors with or without isopropyl myristate overlay. Cell samples from were extracted and mevalonate pathway metabolites and co-factors were analyzed using LC/MS/MS. The objective is to verify that intracellular mevalonate pathway metabolites and co-factors can be detected and that those metabolites and co-factors can be quantified.

Study Design. Cell samples were prepared using a basic extraction method that allows for quantification of coA co-factors and other mevalonate pathway metabolites and co-factors. Using the LC/MS/MS procedure and results described in Example 1, intracellular metabolites and cofactors were identified and quantified. Linearity and reproducibility of the measured relative concentration was also evaluated.

Summary of the Extraction Procedure. Generally, the extraction procedure involves immediately quenching the harvested cells using −80° C. methanol. The mixture is then centrifuged and supernatant is removed. The pellets are then re-suspended with extraction solvent and glass beads. The re-suspended pellets and glass beads are vortexed and then sonicated to break the cells open. The supernatant is collected and subsequent extractions can be performed to maximize recovery of the desired metabolites and co-factors. In some procedures, samples were immediately quenched with −80° C. methanol. After methanol removal by centrifugation, analytes were extracted in 2 rounds with 20 mM ammonium acetate buffer, pH 9.4:methanol (50:50 v/v). Extracts were analyzed by HILIC-MS/MS. Chromatography was performed on a Luna NH2 column (150×2.1, 3μ, Phenomenex) with solvent A (20 mM ammonium acetate buffer, pH 9.4) and solvent B (acetonitrile) with a gradient of 80% o 0% B in 25 min. Mass spectrometer (TSQ quantum ultra, ThermoFisher) was operated in MRM mode in both positive and negative ESI mode to cover all the metabolites and co-factors.

Detailed Protocol. Extraction tubes were prepared by adding 1.6 mL of HPLC grade methanol to pre-induction samples or 0.8 mL of HPLC grade methanol to post-induction samples and then stored overnight at −80° C. An extraction buffer was prepared with internal standards by adding approximately 50 μl of internal standard mixture was to approximately 950 μL of extraction buffer. Extraction tubes were removed from −80° C. and placed on dry ice.

400 or 200 μl of sample (depending on whether it was a pre-induction sample or post-induction sample respectively) was added into extraction tubes. (The sample was poured directly into MeOH and not on the walls of the tube as it would freeze on walls, making it difficult to re-suspend the cells). The tube was inverted 6 times and then stored on dry ice. The sample was then centrifuged immediately (within 2 minutes) in a refrigerated ultracentrifuge at 9000 rcf for 2 minutes and then stored on dry ice. The supernatant was then removed and the pellet was stored on wet ice. The pellet was then re-suspended in 400 μl of extraction solvent (pH 9.4) 20-25 glass beads were added to the re-suspended pellet and vortexed for 2 minutes. The re-suspended pellet was stored on wet ice for 10 min, vortexed for 1 min and then further stored on wet ice for an additional 5 minutes.

After vortexing, the sample was sonicated for 3 minutes in cold water. After sonication, the sample was centrifuged in a refrigerated microcentrifuge at 9000 rcf for 3 minutes at 4° C. Supernatant was transferred to a labeled microcentrifuge tube. The pellet was re-suspended in 400 μl of extraction buffer (pH 9.4) by pipetting and vortexed for 2 minutes. The re-suspended pellet was stored on wet ice for 10 minutes, vortexed for 1 minute and then further stored on wet ice for an additional 5 minutes. After vortexing, the sample was sonicated for 3 minutes in cold water. After sonication, the sample was centrifuged in a refrigerated microcentrifuge at 9000 rcf for 3 minutes at 4° C. Supernatant was combined with the supernatant from the previous extraction.

The combined supernant was vortexed for 1 minute. Samples were immediately diluted for LC analysis in fresh 1.5 mL tubes. 3× dilution were performed for negative mode runs: 100 μl of extract was added to 200 μl of HPLC grade methanol. 5× dilution were performed for positive mode runs: 100 μl of extract was added to 400 μl of methanol with 0.125% formic acid. Diluted samples were stored on wet ice for 5 minutes. The samples were centrifuged at 18,000 rcf for 3 minutes at 4° C. 250 μl was transferred from each tube to a corresponding vial for LC analysis and stored on dry ice until analysis or frozen at frozen at −80° C.

If the cells were grown in the presence of a hydrophobic overlay (e.g. methyl oleate or isopropyl myristate), the an optional washing step can be added. This washing step could occur after the quenching reaction when the quenching mixture is centrifuged. A washing solvent such as chloroform can be added to the cell pellet. Alternatively, the washing step could occur prior to the basic supernatant is divided into aliquots for analysis. For example, an amount of cold chloroform can be added and then centrifuged. After centrifugation, the top most layer is removed and discarded. The supernatant can then be processed as previously described. This optional washing step allows for better reproducibility in samples where cells are grown in the presence of a hydrophobic overlay.

Storage of final extract. If necessary, final extracts were stored at −80° C. for 6 days. The diluted (final methanol dilution) extracts were stored in eppendorf tubes (not the LC vials). On the day of analysis, the frozen diluted extracts were thawed on wet ice and centrifuged at 18,000 rcf for 4 minutes at 4° C. 250 μl of the sample was then transferred to LC vials.

Sample Analysis. Samples are analyzed using LC/MS/MS as described in Example 1.

Figure 3:
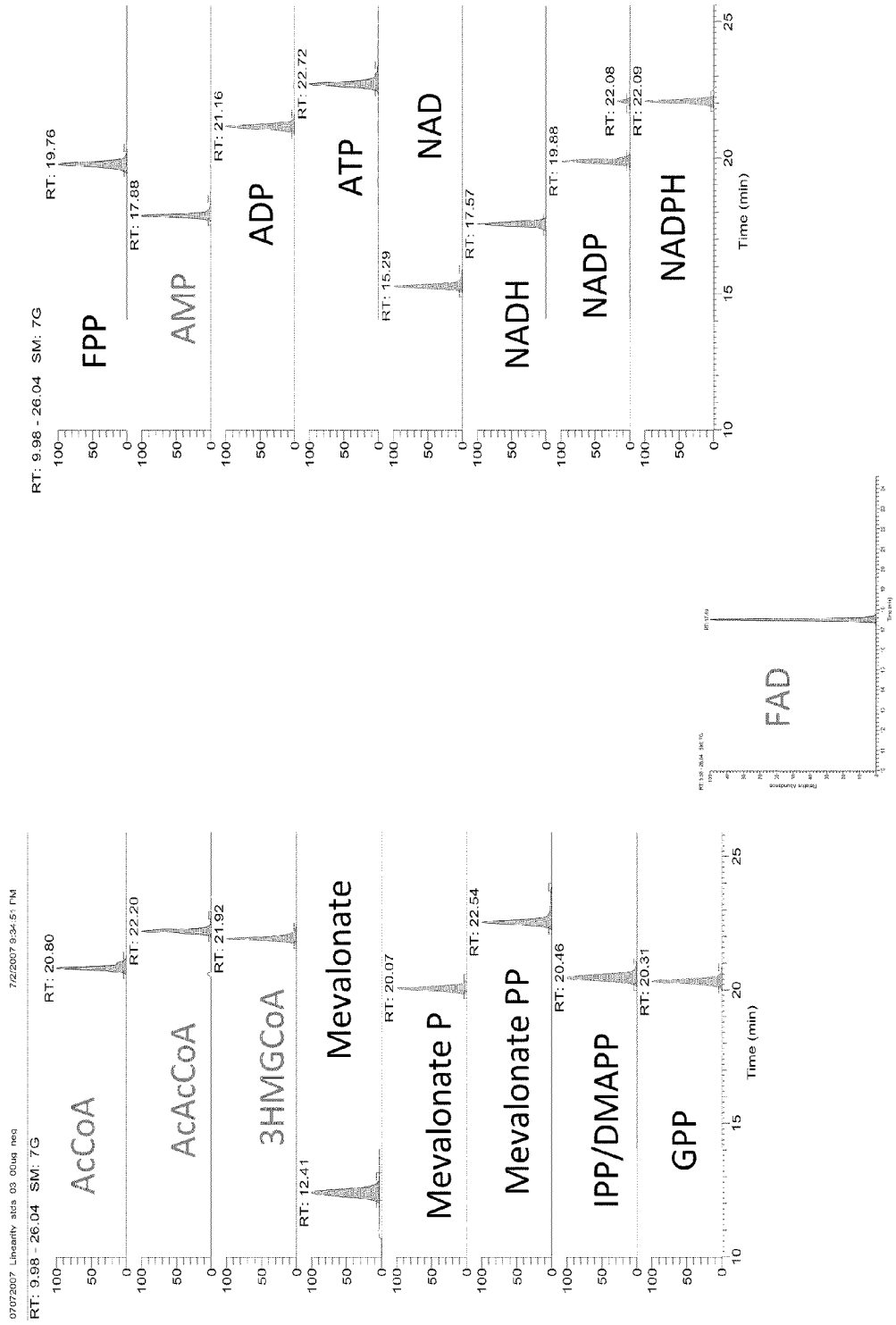
FIG. 3 shows LC/MS/MS data collected from MEV pathway standards and demonstrates detectability and defined peak shape for MEV pathway metabolites and co-factors.

Results. Cells were extracted using the protocol described above and then analyzed using LC/MS/MS as described in Example 1. Illustrated results are shown in FIG. 3. Each of the mevalonate pathway metabolites and co-factors showed a linear relationship between peak area and concentration of the analyte in the sample and the calculated R2 values are close to 1 (ranged from 0.894 to 0.999). As shown by Tables 4 and 5, the inventive methods showed good intra-day and inter-day reproducibility. Overall extraction reproducibility was determined to be 5-10%.

TABLE 4

Intra-day reproducibility (3 injections in a day)

|  | L_RSD_Intra-day (0.3 ug/ml) | M_RSD_Intra-day (1.5 ug/ml) | H_RSD_Intra-day (10 ug/ml) |
| --- | --- | --- | --- |
| Acetoacetyl CoA | 3.60 | 4.44 | 3.39 |
| GPP | 20.65 | 3.16 | 1.07 |
| TTP | 14.00 | 2.43 | 7.79 |

TABLE 5 inter-day reproducibility (3 days)

|  | L_RSD_Inter-day | M_RSD_Inter-day | H_RSD_Inter-day |
| --- | --- | --- | --- |
| Acetoacetyl CoA | 19.83 | 9.64 | 4.79 |
| GPP | 16.78 | 8.02 | 11.16 |
| TTP | 25.72 | 9.16 | 9.29 |

Example 3

The extraction method was performed at multiple conditions to achieve high stability and recovery of MEV pathway metabolites and co-factors. Efforts were made to ensure stability and recovery of CoA containing metabolites, non-coA containing metabolites, and co-factors.

Study Design. The following parameters were investigated for highest stability and recovery of MEV pathway metabolites and co-factors: extraction solvent pH, ratio of extraction solvent to broth, number of extractions, acidification of the extracted metabolites.

Figure 4A:
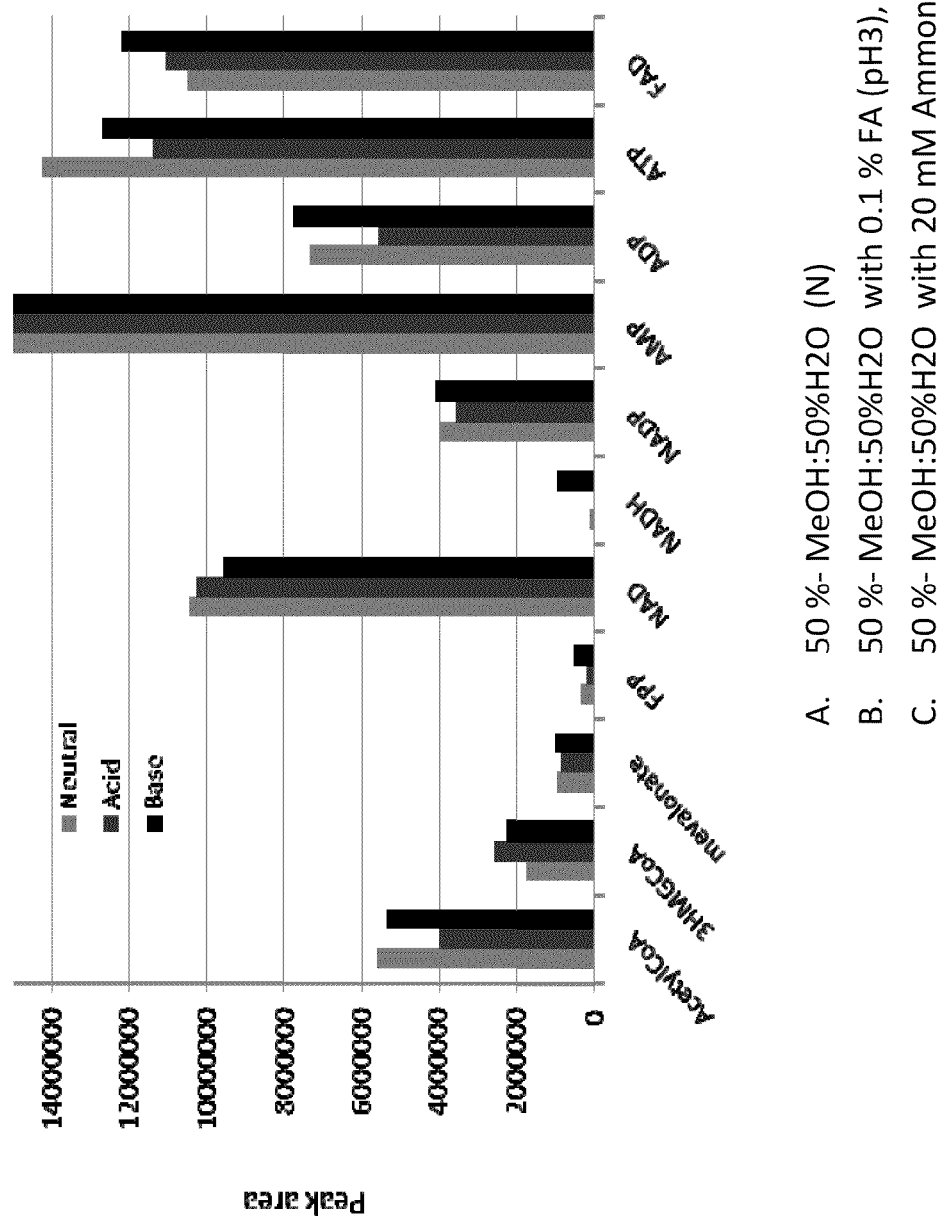
FIGS. 4A-C shows effects of using a basic, neutral, or acidic extraction buffer on recovery of intracellular metabolites and co-factors.
Figures 4B, 4C:
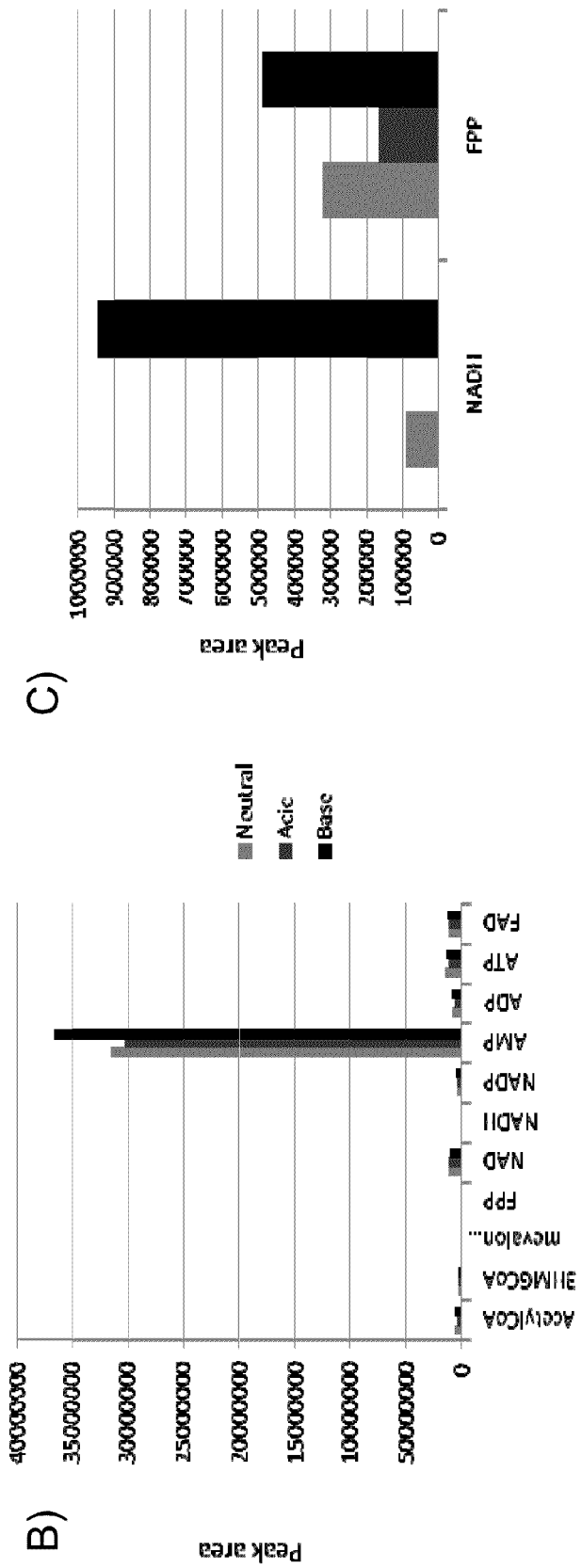

Results. The effects of extraction solvent pH on recovery of metabolites and co-factors are shown in FIG. 4. Higher recovery of several co-factors and metabolites, including NADH and FPP, were observed when a basic extraction buffer was used. A higher recovery level of both NADP and NADPH was observed when the broth to extraction solvent ratio was 1:2

(versus a 1:1 and 1:4). Higher recovery of the MEV pathway metabolites and co-factors was observed after two extractions using 50% methanol and 50% water with 20 mM ammonium acetate (pH 9.4) in comparison to a single extraction or three extractions.

Figure 5:
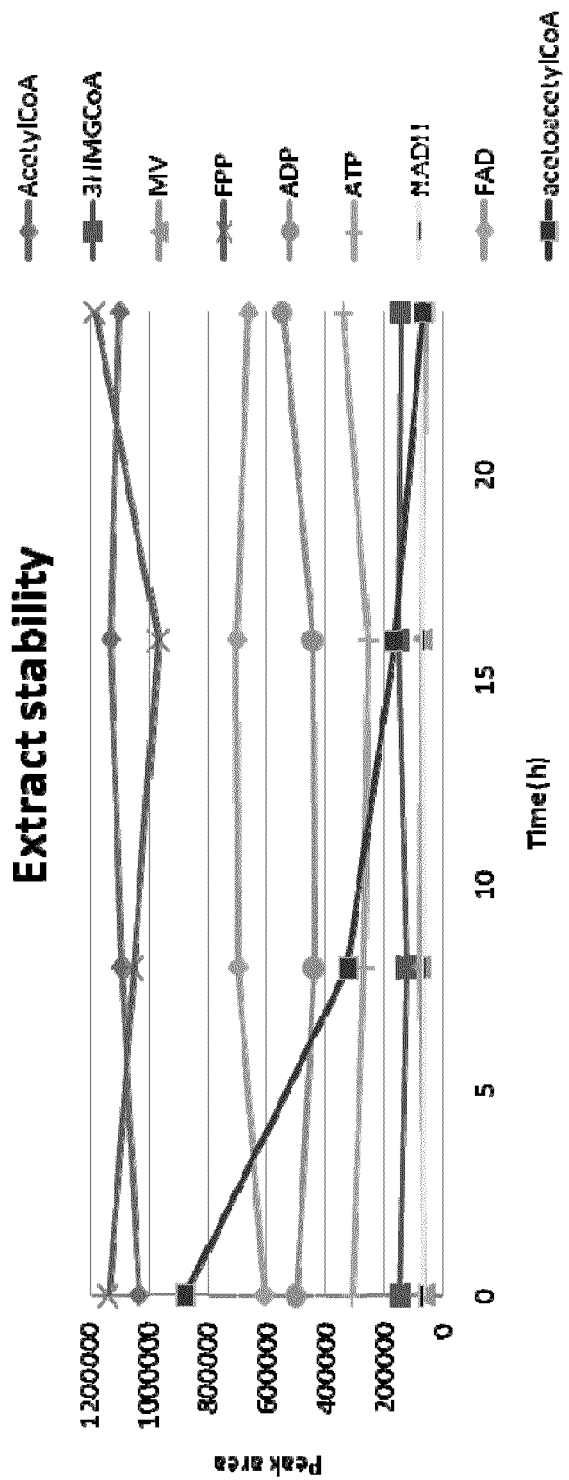
FIG. 5 shows stability of metabolites and co-factors in cell-extracts after extraction. As it can be seen, acetoacetyl CoA degrades with time.
Figure 6:
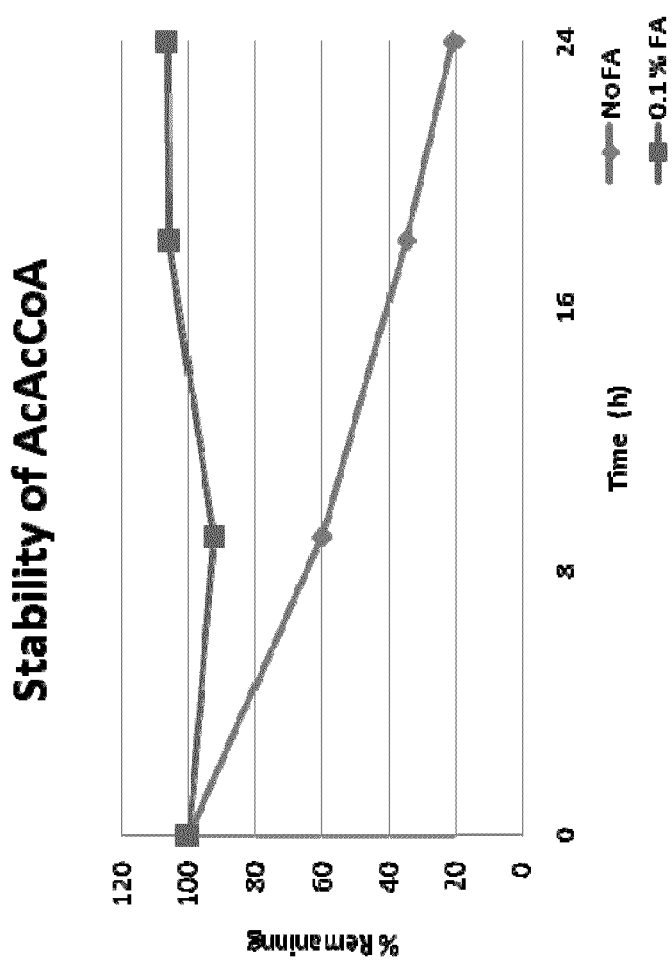
FIG. 6 shows the stability of acetoacetyl CoA with and without extract acidification (e.g. such as by the addition of 0.1% formic acid (FA)).

The stability of Acetyl-CoA, HMG-CoA, Mevalonate, FPP, ADP, ATP, NADH, FAD, and AcAc-CoA is shown over time in FIG. 5. The amount of AcAc-CoA recovered after 20 hours is significantly lower than after 0 hours. The effect of formic acid addition to the extract for acidification is shown in FIG. 6. AcAc-CoA is stable in the acidified extract for at least 24 hours.

Example 4

Quenching of cells was evaluated to ensure proper final temperature after addition of −80° C. methanol to broth and to evaluate how much metabolite was lost due to the quenching process.

Study Design. Temperature of a mixture of 30° C. water and −80° C. methanol was measured after mixing ratios of water to methanol from 1:1 to 1:4. An optimal ratio for water to methanol was evaluated for recovery of MEV pathway metabolites and co-factors using LC/MS/MS.

Results. The various rations of water and methanol results in different temperatures from −5° C. to −30° C. A water to methanol ratio of 1:4 results in a temperature of approximately −30° C. and use of this ratio results in no significant loss of analytes during the quenching step.

Quenching of cells was evaluated to ensure proper final temperature after addition of −80° C. methanol to broth and to evaluate how much metabolite was lost due to the quenching process.

Study Design. Temperature of a mixture of 30° C. water and −80° C. methanol was measured after mixing ratios of water to methanol from 1:1 to 1:4. An optimal ratio for water to methanol was evaluated for recovery of MEV pathway metabolites and co-factors using LC/MS/MS.

Figure 7:
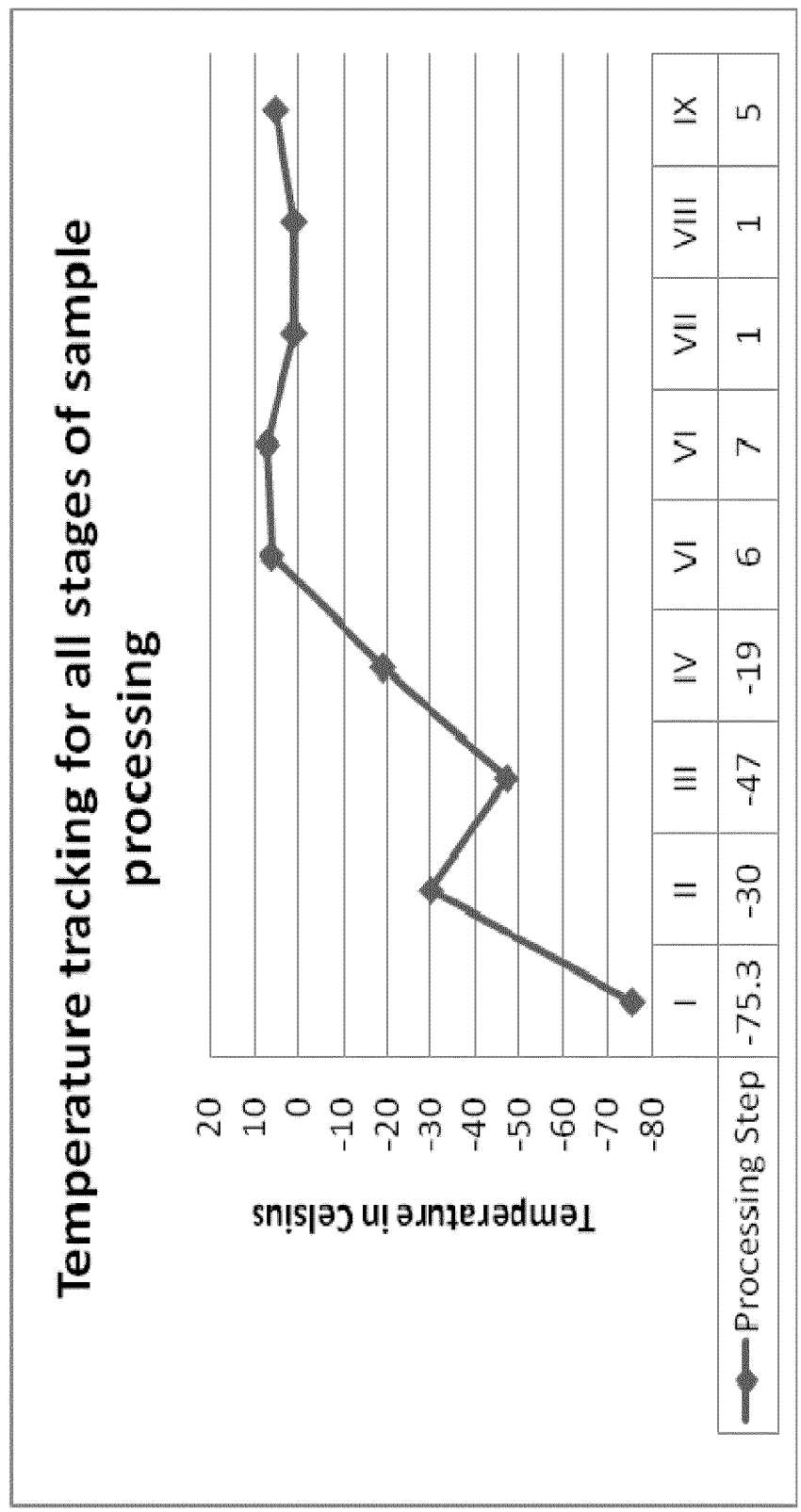
FIG. 7 shows the effect of each processing step to the temperature (in Celsius) of the sample: Processing step I—quenching solvent on dry ice; II—solvent and broth at quenching; III—after 1 minute on dry ice; IV—after centrifugation at −10° C.; V after extraction solvent was added; VI, sonication; VII—after 10 minutes on wet ice; VIII—after 5 minutes on wet ice; IX—after centrifugation at −4° C.
Figure 8A:
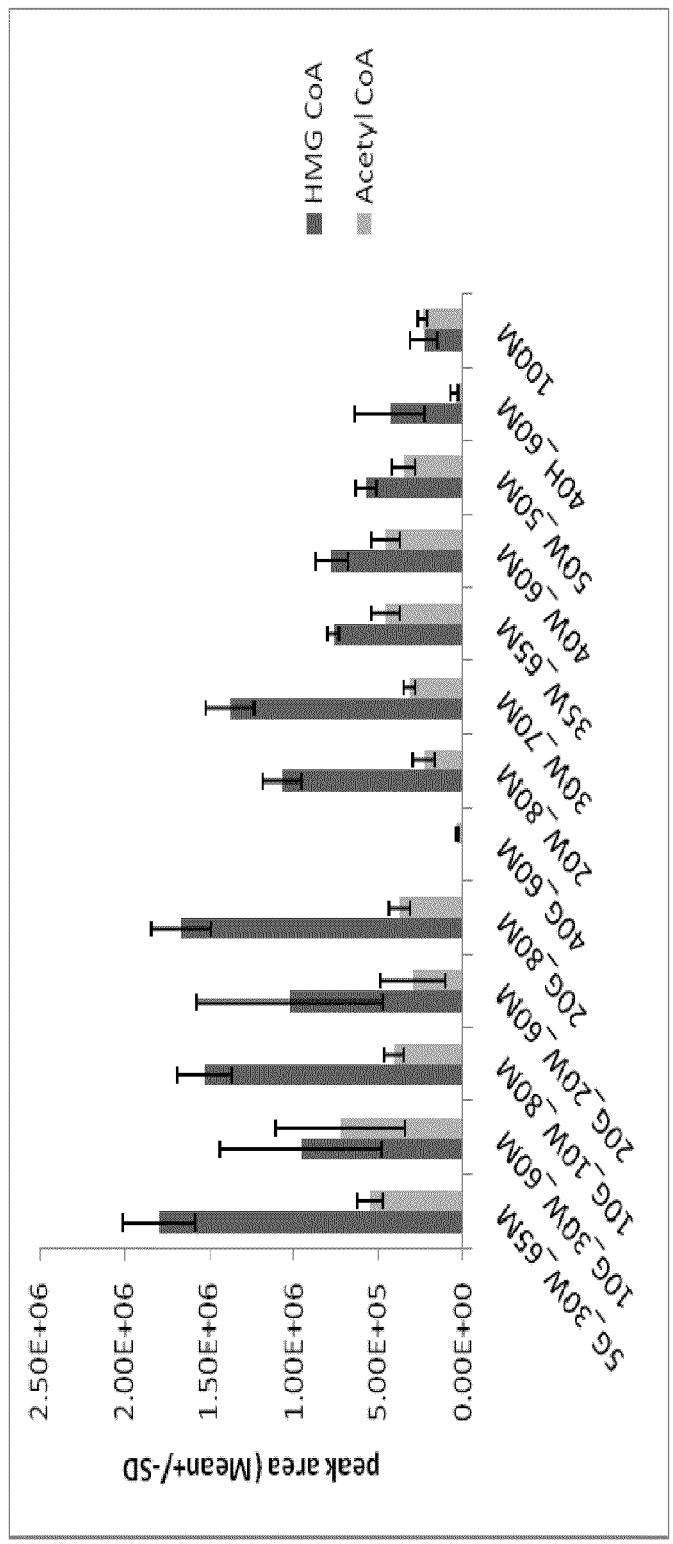
FIGS. 8A-D illustrates the effects of the addition of water or glycerol or both to 100% methanol on the detection of representative intracellular metabolites. The best quenching solvent in this experiment was determined to be 65% methanol, 30% water and 5% glycerol.
Figure 8B:
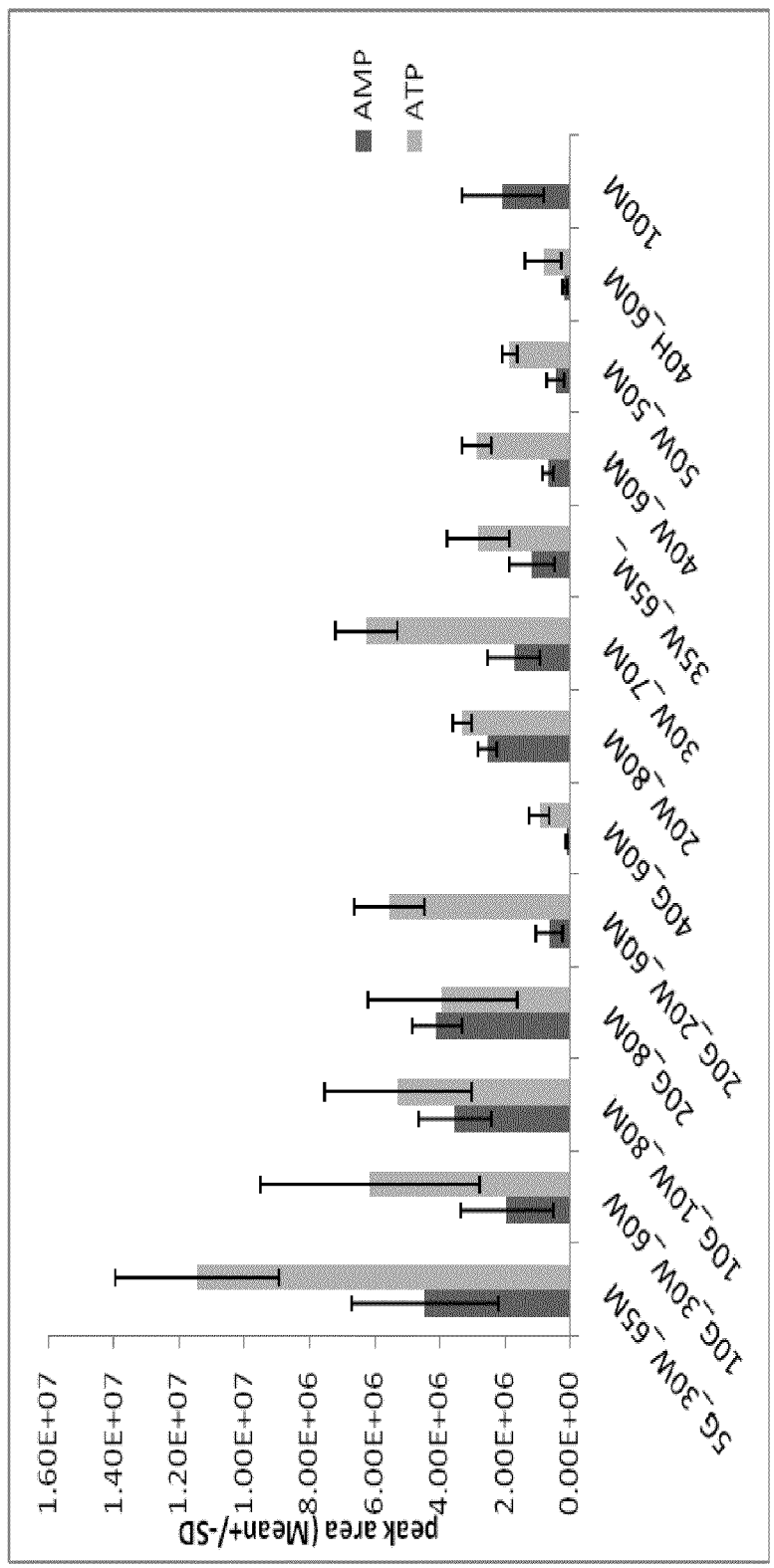
Figure 8C:
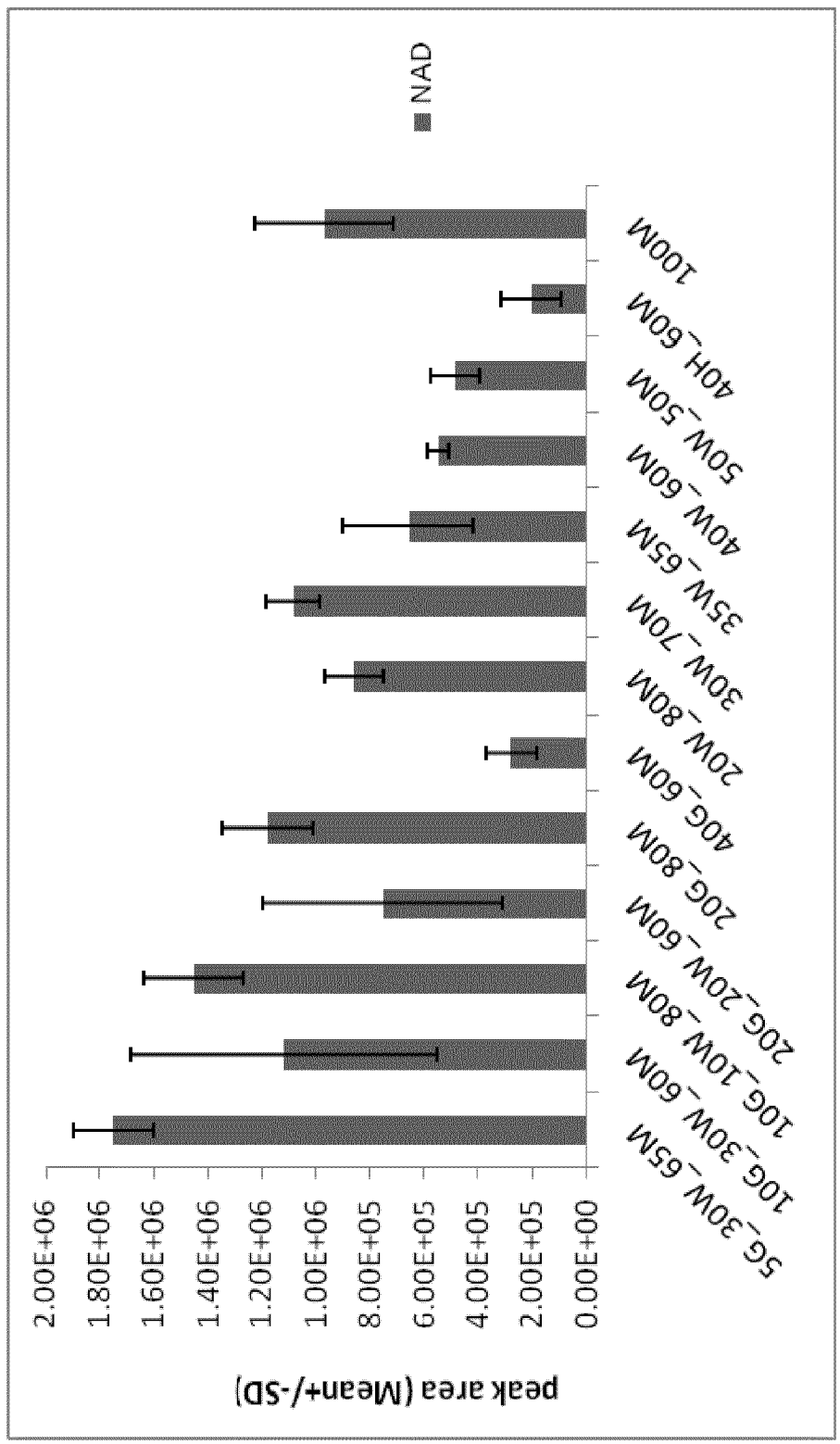
Figure 8D:
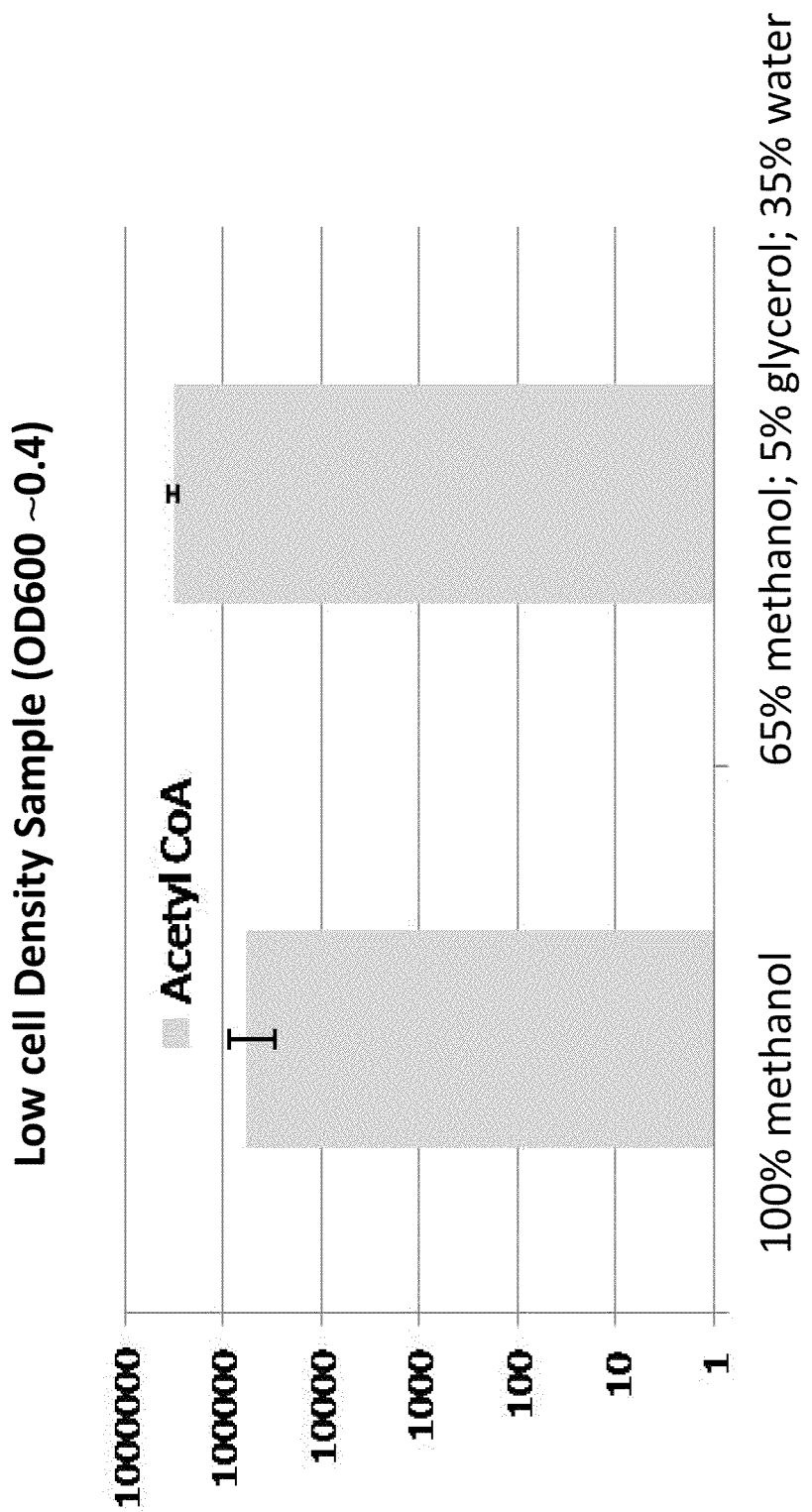

Results. The various ratios of water and methanol results in different temperatures from −5° C. to −30° C. A water to methanol ratio of 1:4 (broth to quenching solvent) results in a temperature of approximately −30° C. and use of this ratio results in no significant loss of analytes during the quenching step. FIG. 7 shows the temperature of the sample for the various processing step.

Example 5

Various different quenching solvents were tested to revisit whether a 100% methanol was the best quenching solvent. Based on fluidity and ease of handling at −80° C., methanol and glycerol were chosen. Thirteen different quenching solvent mixtures were tested:

5% glycerol; 30% water; 65% methanol
10% glycerol; 30% water; 60% methanol
10% glycerol; 10% water; 80% methanol
20% glycerol; 20% water; 60% methanol
20% (v/v) glycerol/methanol
40% (v/v) glycerol/methanol
20% (v/v) water/methanol
30% (v/v) water/methanol
35% (v/v) water/methanol
40% (v/v) water/methanol
50% (v/v) water/methanol
40% (v/v) HEPES/methanol
100% methanol Study Design. Cell sampling was accomplished by quenching requisite amounts of yeast culture in −80° C. solvent. For optical densities below 1.0 OD, 3 mL of broth was quenched in 12 mL solvent. For optical densities greater than 1.0 OD, 0.4 mL of broth was quenched in 1.6 mL solvent. Samples were immediately centrifuged at 4500 rpm for 3 minutes at −7° C. for low OD, while high OD samples were centrifuged at 9000 rcf for 3 minutes at −10° C. After centrifugation, supernatant was removed analyzed for potential intracellular metabolite leakage. Sample pellets were kept on wet ice, where 200 μl internal standard spiked extraction buffer (50 μL internal standard per mL 20 mM ammonium acetate buffer) and glass beads were added and vortexed. Samples were sonicated in a wet ice bath for 3 minutes and placed on wet ice for 10 minutes, vortexed and subject to an additional 5 minutes on ice. Samples were then centrifuged at 9,000 rcf for 3 minutes, at 4° C. Extract was removed and the extraction procedure was repeated. Extract was pooled, diluted twice with methanol and analyzed by LCMSMS.

Results. As it can be seen from FIGS. 8A-8D, the best quenching solvent was determined to be 5% glycerol; 30% water; 65% methanol. Prior art quenching solvents have described the use of buffered or un-buffered 60% methanol (at or below −40° C.) which is a standard way of rapidly arresting metabolic activity. However, because of concerns of the likelihood of leakages of intra-celluar metabolites during the quenching reaction, quenching solvents that minimize such leakage have been explored. For example, one type of such solvents are glycerol-containing ones where glycerol is present in high concentrations (greater than 30%). A commonly used example is 40% glycerol in Hepes buffer. However, the use of this solvent requires that quenching occur at −23° C. as the solvent mixture freezes below this temperature. Moreover, although it is possible to decrease the freezing point by the addition of methanol, the high glycerol concentration (e.g. greater than 30%) makes the analysis of extracellular metabolites difficult, if not impossible due to chemical derivatization issues as well as signal interference by glycerol in gas chromatography analysis.

Methanol water combinations suffer from many of the same issues as glycerol saline combinations. Low freezing point and metabolite leakage prevent this from being a quenching solvent if one is interested in detecting a wide range of metabolites.

Figure 9:
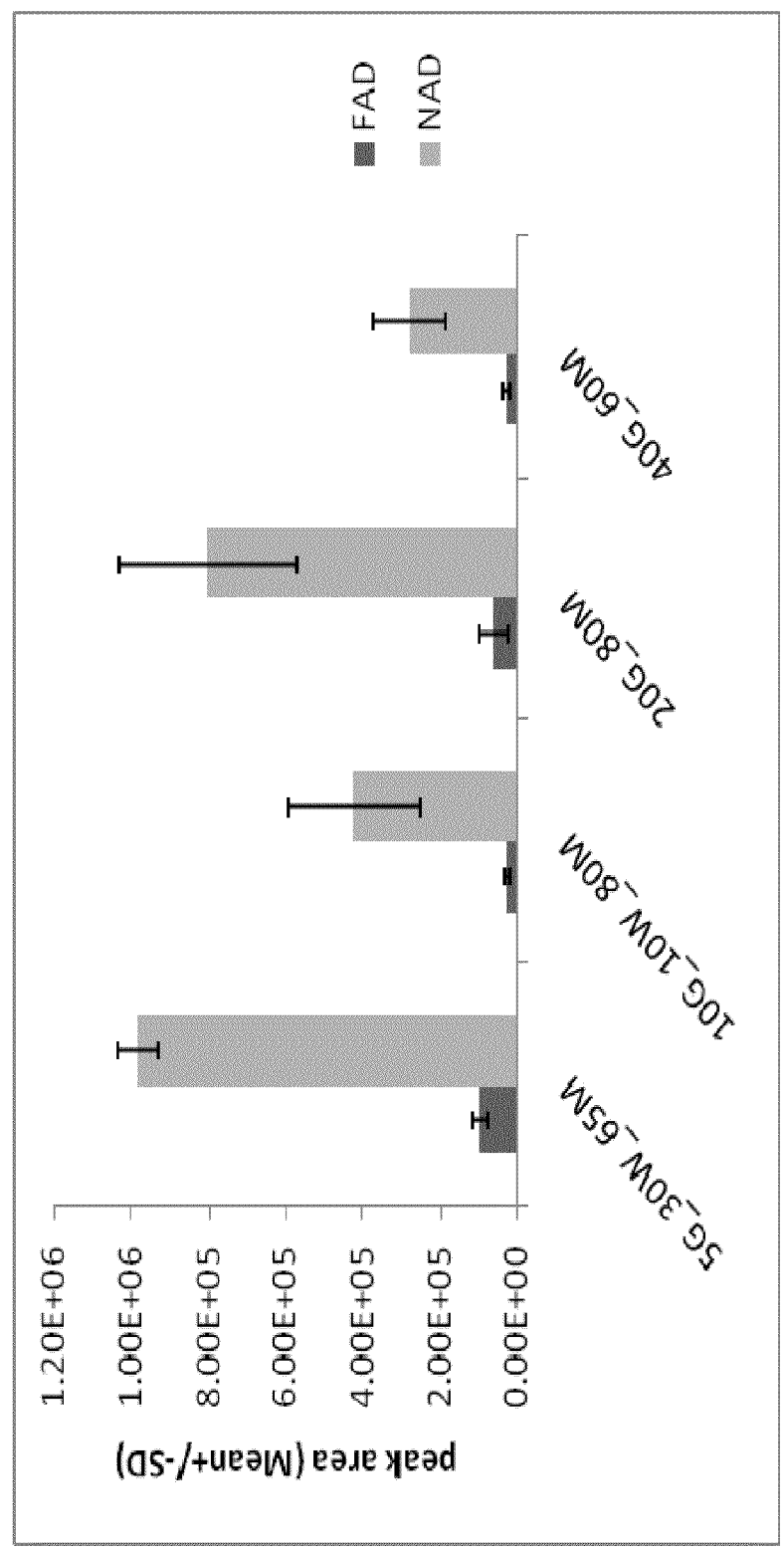
FIG. 9 illustrate the effects of various amounts of glycerol to the detection of FAD and NAD. As it can be seen, better detection was observed with less than 40% glycerol (such as 20%, 10%, and 5%) than with 40% glycerol.

100% methanol is an excellent quenching solvent under most circumstances, particularly in high cell density situations such as high density fermentations (optical density$_{600}$ 30-200). However, for low density fermentors and shake flask models (optical density$_{600}$ 0.3-15), the metabolite signals are highly variable and there is significant ion suppression. In these low cell density situations, the addition of glycerol appears to improve signal detection by reducing ion suppression effect. In other words, the signal intensity is significantly removed by less salt precipitation. As it can be seen by FIG. 9, 5% glycerol is sufficient to avoid salt precipitation and significantly improve signal quality. However, up to 20% glycerol can be used without introducing lengthy centrifugation step without significant adhering to sample vials.

Metabolites. The metabolites analyzed by this method using 5% glycerol; 30% water; 65% methanol as the quenching solvent include aminoacids, nucleoside bases, nucleosides, nucleoside monophosphates, nucleoside di/triphosphates, CoAs, carboxylic acids and redox-electron carriers and precursors. The amino acids include: alanine, arginine, asparagines, glutamate, glutamine, histidine, lysine, methionine, phenylalanine, proline, serine, threonine, tryptophan, tyrosine, and valine. The nucleoside bases include:

adenine, cytosine, guanine, and uracil. The nucleosides include: adenosine, cytidine and guanosine. The nucleoside monophosphates include: AMP, CMP, cyclic-AMP, dGMP, and GMP. The nucleoside di/triphosphates include: ADP, ATP, CDP, CTP, GTP, TTP, and UDP. The CoAs include: HMG-CoA, acetoacetyl CoA, acetyl-CoA, CoA, dephospho-CoA, and malonyl CoA. The carboxylic acids include: citrate, fumarate, malate, and succinate. The redox-electron-carriers and precursors include: FAD, FMN, NAD+, NADPH, oxidized glutathione, and reduced glutathione.

Example 6

The sensitivity of the method of Example 1 could be improved by moving the analysis of certain metabolites from negative to positive mode. Metabolites NAD, NADH, NADP, NADPH, ATP and ADP were moved from negative to positive mode ionization for mass spectrometry analysis. Table 6 details the internal standards, metabolites and the mode of analysis.

TABLE 6

Metabolite and Method of Analyses

| Metabolite | Internal Standard | Mode of Analysis |
|---|---|---|
| AMP, FAD, GSH, GSSG | $^{13}C_{10}{}^{15}N_5$ AMP | positive |
| AcCoA, Acetoacetyl CoA, 3-HMGCoA | $^{13}C_3$ malonyl CoA | positive |
| NAD, NADH, NADP | NHD | positive |
| NADPH | NHDPH | Positive |
| ATP, ADP | $^{13}C_{10}{}^{15}N_5$ ATP | positive |
| MVP | Hydroxyl-FP | negative |
| Mevalonate | $D_7$ mevalonate | Negative |
| MVPP, IPP, DMAPP, GPP, FPP | Thio-FPP | negative |

Figure 10:
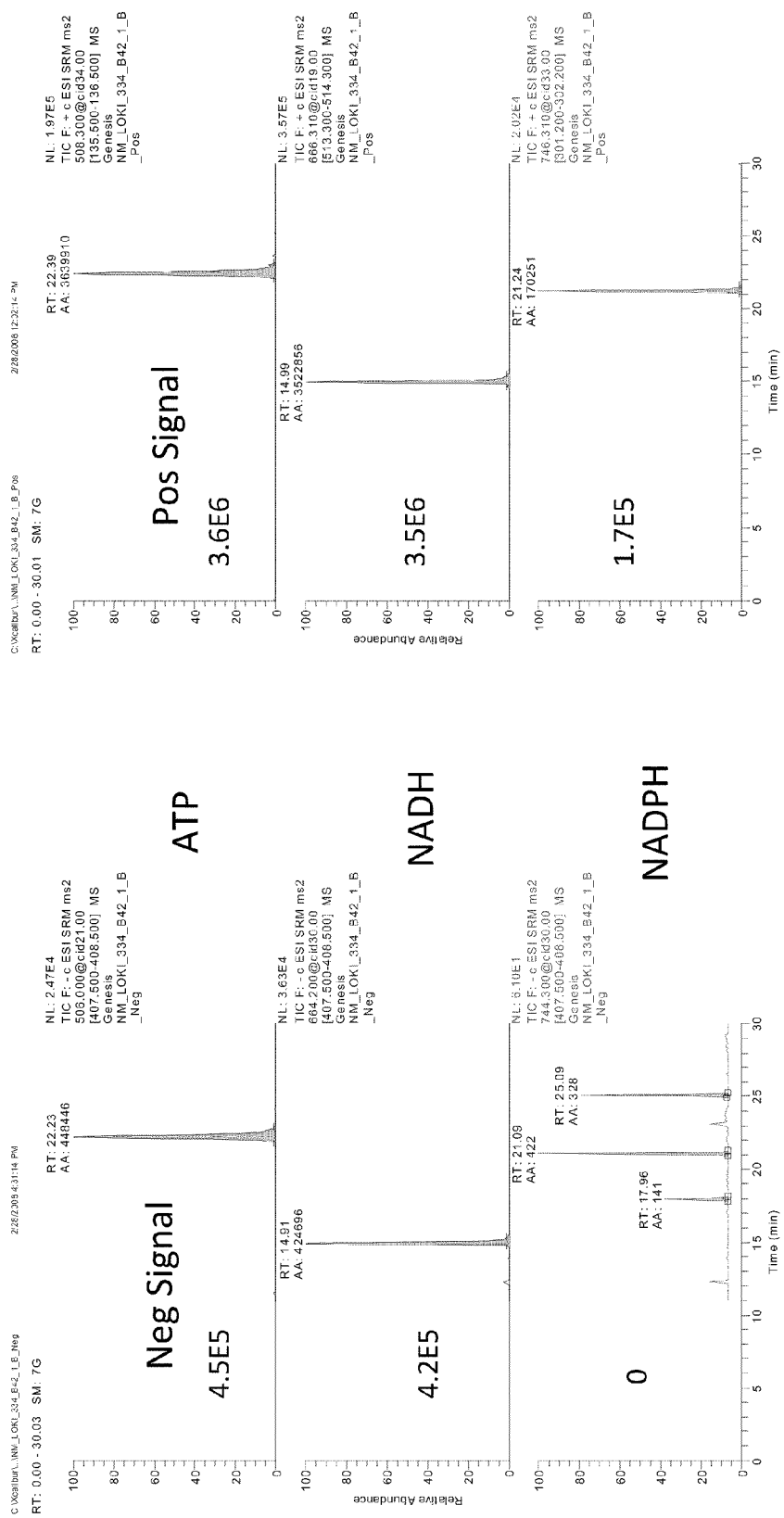
FIG. 10 compares the analysis of ATP, NADH and NADPH in negative and positive modes.

FIG. 10 shows the improved sensitivity of ATP, NADH, and NADPH when the method of analysis is switched from negative to positive mode.

What is claimed is:

1. A method of quantitating a cofactor and a mevalonate pathway metabolite, comprising:
    (a) providing an extract of a cell comprising a cofactor and a mevalonate pathway metabolite, wherein the extract exhibits a pH value of 8 or greater; and
    (b) quantitating said cofactor and said metabolite from said extract.

2. A method of quantitating a cofactor and a mevalonate pathway metabolite, comprising:
    (a) quenching cell metabolism in a plurality of cells having at least one cofactor and metabolite by contacting the cells with a quenching solvent resulting in a first mixture, wherein the first mixture has a temperature that is equal to or less than about −25° C.;
    (b) adding an extraction solvent to the first mixture resulting in a second mixture wherein the pH of the second mixture has a pH value of 8 or greater; and
    (c) quantitating said cofactor and said metabolite from the second mixture.

3. The method in claim 2 wherein the quenching solvent is a liquid at −80° C.

4. The method in claim 2 wherein the quenching solvent comprises methanol and glycerol and remains a liquid at −80° C.

5. The method of claim 2 wherein the metabolite includes at least acetoacetyl CoA and the method further comprises dividing the second mixture into at least two aliquots, wherein one of the aliquot is acidified and used to quantify acetoacetyl CoA and the other aliquot is used to quantitate a cofactor or metabolite that is not acetoacetyl CoA.

6. The method of claim 1 or 2, wherein the cofactor is selected from the group consisting of NAD$^+$, NADP$^+$, NADH, NADPH, AMP, ADP, and ATP, and wherein the metabolite is selected from the group consisting of farnesyl pyrophosphate, geranyl pyrophosphate, isopentenyl pyrophosphate, dimethylallyl pyrophosphate, mevalonate, mevalonate phosphate, and mevalonate pyrophosphate.

7. The method of claim 1 or 2, wherein the step of quantitating is effected by mass spectrometry.

8. The method of claim 1 or 2, wherein the step of quantitating is effected by liquid chromatography in conjunction with mass spectrometry.

9. The method of claim 1 or 2, wherein the cell is prokaryotic.

10. The method of claim 1 or 2, wherein the cell is eukaryotic.

11. The method of claim 1 or 2, wherein the cell is a bacterial cell.

12. The method of claim 1 or 2, wherein the cell is a yeast cell.

13. A method comprising:
    (a) quenching cell metabolism in a plurality of cells having at least one cofactor and metabolite by contacting the cells with a quenching solvent resulting in a first mixture, wherein the first mixture has a temperature that is equal to or less than about −25° C.;
    (b) separating the cells from the supernatant in the first mixture resulting in a cell pellet;
    (c) isolating the cell pellet;
    (d) adding an extraction solvent to the cell pellet resulting in a second mixture wherein the pH of the second mixture has a pH value of 8 or greater;
    (e) breaking open the cells in the second mixture;
    (f) separating the cell debris from the supernatant in the second mixture;
    (g) dividing the supernatant in the second mixture into at least two aliquots;
    (h) acidifying one of the at least two aliquots; and,
    (i) quantitating the at least one cofactor and metabolite in the at least two aliquots.

14. The method of claim 13, wherein the acidified aliquot is used to quantitate a CoA or ATP and the non-acidified aliquot is used to quantitate a cofactor or metabolite that is not a CoA or ATP.

15. The method of claim 13, wherein the acidified aliquot is used to quantitate acetoacetyl CoA and the non-acidified aliquot is used to quantitate a cofactor or metabolite that is not acetoacetyl CoA.

16. The method of claim 13, wherein the method quantitates each cofactor from the group consisting of NAD+, NADP+, NADH, NADPH, AMP, ADP, and ATP and each metabolite of the mevalonate pathway from the group consisting of farnesyl pyrophosphate, geranyl pyrophosphate, isopentyl pyrophosphate, dimethylallyl pyrophosphate, mevalonate, mevalonate phosphate, and mevalonate pyrophosphate, and wherein the step of quantifying is effected by liquid chromatagraphy in conjunction with mass spectrometry.

17. The method of claim 13, wherein the cofactor and the metabolite are quantitated with a relative standard deviation (RSD) of less than 13%.

* * * * *